US012747487B2

(12) United States Patent
Huang et al.

(10) Patent No.: US 12,747,487 B2
(45) Date of Patent: Sep. 29, 2026

(54) COMPOSITIONS FOR THE TREATMENT OF RHEUMATOID ARTHRITIS AND METHODS OF USING SAME

(71) Applicants: Sanofi Biotechnology, Paris (FR); Regeneron Pharmaceuticals, Inc., Tarrytown, NY (US)

(72) Inventors: Xiaohong Huang, Cambridge, MA (US); Martine Jasson, Paris (FR); Vanessa Marks, Paris (FR); Allen Radin, Tarrytown, NY (US)

(73) Assignees: SANOFI BIOTECHNOLOGY, Gentilly (FR); REGENERON PHARMACEUTICALS, INC., Tarrytown, NY (US)

( * ) Notice: Subject to any disclaimer, the term of this patent is extended or adjusted under 35 U.S.C. 154(b) by 1365 days.

(21) Appl. No.: 17/133,870

(22) Filed: Dec. 24, 2020

(65) Prior Publication Data

US 2021/0230719 A1 Jul. 29, 2021

Related U.S. Application Data

(63) Continuation of application No. 14/350,973, filed as application No. PCT/EP2012/070052 on Oct. 10, 2012, now Pat. No. 10,927,435.

(60) Provisional application No. 61/545,864, filed on Oct. 11, 2011.

(30) Foreign Application Priority Data

Jul. 20, 2012 (EP) .................................... 12305889

(51) Int. Cl.

| | |
|---|---|
| ***G01N 31/00*** | (2006.01) |
| ***A61K 31/42*** | (2006.01) |
| ***A61K 31/4706*** | (2006.01) |
| ***A61K 31/519*** | (2006.01) |
| ***A61K 31/635*** | (2006.01) |
| ***A61K 31/655*** | (2006.01) |
| ***A61K 39/395*** | (2006.01) |
| ***A61K 45/06*** | (2006.01) |
| ***B21D 22/02*** | (2006.01) |
| ***B21J 1/06*** | (2006.01) |
| ***C07K 16/28*** | (2006.01) |
| ***C22C 19/05*** | (2006.01) |
| ***C22F 1/10*** | (2006.01) |
| ***G01N 33/53*** | (2006.01) |
| *A61K 39/00* | (2006.01) |

(52) U.S. Cl.

CPC ............ *C22C 19/058* (2013.01); *A61K 31/42* (2013.01); *A61K 31/4706* (2013.01); *A61K 31/519* (2013.01); *A61K 31/635* (2013.01); *A61K 31/655* (2013.01); *A61K 39/39541* (2013.01); *A61K 39/3955* (2013.01); *A61K 45/06* (2013.01); *B21D 22/022* (2013.01); *B21J 1/06* (2013.01); *C07K 16/2866* (2013.01); *C22C 19/05* (2013.01); *C22F 1/10* (2013.01); *A61K 2039/54* (2013.01); *A61K 2039/545* (2013.01)

(58) Field of Classification Search

None

See application file for complete search history.

(56) References Cited

U.S. PATENT DOCUMENTS

| | | | |
|---|---|---|---|
| 4,997,423 | A | 3/1991 | Okuda et al. |
| 5,016,784 | A | 5/1991 | Batson |
| 5,215,534 | A | 6/1993 | De Harde et al. |
| 5,480,796 | A | 1/1996 | Kishimoto |
| 5,605,690 | A | 2/1997 | Jacobs et al. |
| 5,670,373 | A | 9/1997 | Kishimoto |
| 5,723,120 | A | 3/1998 | Brackenhoff et al. |
| 5,795,965 | A | 8/1998 | Tsuchiya |
| 5,817,790 | A | 10/1998 | Tsuchiya |
| 5,888,510 | A | 3/1999 | Kishimoto |
| 5,888,511 | A | 3/1999 | Skurkovich et al. |
| 5,908,686 | A | 6/1999 | Sudo et al. |
| 6,046,223 | A | 4/2000 | Sponsel et al. |
| 6,086,874 | A | 7/2000 | Yoshida et al. |
| 6,261,560 | B1 | 7/2001 | Tsujinaka et al. |
| 6,286,699 | B1 | 9/2001 | Sudo |
| 6,410,691 | B1 | 6/2002 | Kishimoto |
| 6,629,949 | B1 | 10/2003 | Douglas |
| 6,632,927 | B2 | 10/2003 | Adair |
| 6,645,635 | B2 | 11/2003 | Murakai |
| 6,659,982 | B2 | 12/2003 | Douglas et al. |
| 6,670,373 | B1 | 12/2003 | Bonjouklian et al. |
| 6,692,742 | B1 | 2/2004 | Nakamura et al. |

(Continued)

FOREIGN PATENT DOCUMENTS

| | | |
|---|---|---|
| BR | PI0712224-1 A2 | 1/2012 |
| CN | 103476793 A | 12/2013 |

(Continued)

OTHER PUBLICATIONS

Smolen et al (Lancet, 2008, vol. 371, pp. 987-997). (Year: 2008).*
Strand et al (Rheumatology 2006, vol. 45, pp. 1505-1513). (Year: 2006).*
Clinical Trial (NCT01217814 dated Feb. 2, 2010) (Year: 2010).*
Clinical Trial (NCT01061736 dated Oct. 7, 2010, filed on IDS submitted May 15, 2024) (Year: 2010).*
Emery et al. Ann Rheum Dis 2008;67:1516-1523. Published Online Jul. 14, 2008 (Year: 2008).*
U.S. Appl. No. 13/043,617, filed Oct. 25, 2011, Stevens et al.

(Continued)

*Primary Examiner* — Lisa V Cook

(74) *Attorney, Agent, or Firm* — LATHROP GPM LLP; James H. Velema, Esq.; Judith L. Stone-Hulslander

(57) ABSTRACT

The present invention provides compositions and methods of treating and improving the symptoms of rheumatoid arthritis using an antibody or antigen-binding fragment thereof that specifically binds human interleukin-6 receptor (hIL-6R) with a DMARD.

24 Claims, 3 Drawing Sheets

Specification includes a Sequence Listing.

(56) References Cited

U.S. PATENT DOCUMENTS

| | | | | |
|---|---|---|---|---|
| 6,723,319 | B1 | 4/2004 | Ito et al. | |
| 7,226,554 | B2 | 6/2007 | Sudo et al. | |
| 7,320,792 | B2 | 1/2008 | Ito et al. | |
| 7,479,543 | B2 | 1/2009 | Tsuchiya et al. | |
| 7,521,052 | B2 | 4/2009 | Okuda et al. | |
| 7,582,298 | B2 | 9/2009 | Stevens | |
| 8,043,617 | B2 | 10/2011 | Stevens et al. | |
| 8,080,248 | B2 * | 12/2011 | Radin | C07K 16/2866 424/143.1 |
| 8,183,014 | B2 | 5/2012 | Stevens et al. | |
| 8,192,741 | B2 * | 6/2012 | Radin | A61K 31/519 424/143.1 |
| 8,440,890 | B1 | 5/2013 | Carlone, Jr. et al. | |
| 8,568,721 | B2 * | 10/2013 | Radin | A61K 31/655 424/143.1 |
| 8,709,409 | B2 | 4/2014 | Okuda et al. | |
| 8,869,904 | B2 | 10/2014 | Jani | |
| 8,895,521 | B2 | 11/2014 | Klinman et al. | |
| 9,139,646 | B2 | 9/2015 | Solinger et al. | |
| 9,173,880 | B2 | 11/2015 | Dix et al. | |
| 9,248,242 | B2 | 2/2016 | Verespe et al. | |
| 9,308,256 | B2 * | 4/2016 | Radin | A61K 38/191 |
| 9,427,531 | B2 | 8/2016 | Hourmand et al. | |
| 9,566,395 | B2 | 2/2017 | Dennt et al. | |
| 9,884,916 | B2 | 2/2018 | Stevens | |
| 9,943,594 | B2 * | 4/2018 | Jasson | A61K 31/635 |
| 9,951,130 | B2 | 4/2018 | Schmidt et al. | |
| 10,072,086 | B2 | 9/2018 | Dix | |
| 10,231,981 | B2 | 3/2019 | Zhang et al. | |
| 10,927,435 | B2 * | 2/2021 | Huang | A61K 31/519 |
| 10,968,278 | B2 | 4/2021 | Sridhara Sundaram et al. | |
| 11,498,969 | B2 | 11/2022 | Baret-Cormel et al. | |
| 12,297,279 | B2 | 5/2025 | Boklage et al. | |
| 2002/0187150 | A1 | 12/2002 | Mihara et al. | |
| 2003/0092606 | A1 | 5/2003 | L'Italien et al. | |
| 2003/0113316 | A1 | 6/2003 | Kaisheva et al. | |
| 2003/0190316 | A1 | 10/2003 | Kakuta et al. | |
| 2004/0071706 | A1 | 4/2004 | Ito et al. | |
| 2004/0115197 | A1 | 6/2004 | Yoshizaki et al. | |
| 2004/0197324 | A1 | 10/2004 | Liu et al. | |
| 2004/0202658 | A1 | 10/2004 | Benyunes | |
| 2004/0219156 | A1 | 11/2004 | Goldenberg et al. | |
| 2005/0142635 | A1 | 6/2005 | Tsuchiya et al. | |
| 2005/0238644 | A1 | 10/2005 | Mihara et al. | |
| 2006/0078531 | A1 | 4/2006 | Sota | |
| 2006/0078532 | A1 | 4/2006 | Omoigui | |
| 2006/0078533 | A1 | 4/2006 | Omoigui | |
| 2006/0177436 | A1 | 8/2006 | Ghilardi et al. | |
| 2006/0251653 | A1 | 11/2006 | Okuda et al. | |
| 2006/0275294 | A1 | 12/2006 | Omoigui | |
| 2006/0292147 | A1 | 12/2006 | Yoshizaki et al. | |
| 2007/0036785 | A1 | 2/2007 | Kishimoto et al. | |
| 2007/0036788 | A1 | 2/2007 | Sheriff et al. | |
| 2007/0098714 | A1 | 5/2007 | Nishimoto et al. | |
| 2007/0143168 | A1 | 6/2007 | Stevens et al. | |
| 2007/0148169 | A1 | 6/2007 | Yoshizaki et al. | |
| 2007/0280945 | A1 | 12/2007 | Stevens | |
| 2008/0124325 | A1 | 5/2008 | Ito et al. | |
| 2008/0131374 | A1 | 6/2008 | Medich et al. | |
| 2008/0145367 | A1 | 6/2008 | Bove et al. | |
| 2008/0269467 | A1 | 10/2008 | Allan et al. | |
| 2009/0082288 | A1 | 3/2009 | Klinman et al. | |
| 2010/0316627 | A1 | 12/2010 | Stevens et al. | |
| 2010/0316636 | A1 * | 12/2010 | Radin | A61K 39/39558 424/130.1 |
| 2011/0098450 | A1 | 4/2011 | Igawa et al. | |
| 2011/0171241 | A1 | 7/2011 | Dix et al. | |
| 2011/0245473 | A1 | 10/2011 | Igawa et al. | |
| 2012/0003697 | A1 | 1/2012 | Stevens et al. | |
| 2012/0171123 | A1 | 7/2012 | Medich et al. | |
| 2012/0258098 | A1 | 10/2012 | Radin et al. | |
| 2012/0301460 | A1 | 11/2012 | Bao et al. | |
| 2013/0014958 | A1 | 1/2013 | Jani | |
| 2013/0149310 | A1 | 6/2013 | Jasson et al. | |
| 2014/0255390 | A1 | 9/2014 | Radin et al. | |
| 2014/0302053 | A1 | 10/2014 | Huang et al. | |
| 2015/0050277 | A1 | 2/2015 | Peters et al. | |
| 2016/0002341 | A1 | 1/2016 | Dix et al. | |
| 2016/0220675 | A1 | 8/2016 | Abrahmson | |
| 2016/0229916 | A1 | 8/2016 | Stevens et al. | |
| 2016/0280782 | A1 | 9/2016 | Huang et al. | |
| 2016/0281106 | A1 | 9/2016 | Kim et al. | |
| 2017/0166646 | A1 | 6/2017 | Sridhara Sundaram et al. | |
| 2017/0198045 | A1 | 7/2017 | Johnson et al. | |
| 2017/0252434 | A1 | 9/2017 | Joseph et al. | |
| 2017/0360807 | A1 | 12/2017 | Zhang et al. | |
| 2018/0296670 | A1 | 10/2018 | Jasson et al. | |
| 2019/0002574 | A1 | 1/2019 | Dix et al. | |
| 2019/0100585 | A1 | 4/2019 | Bauer et al. | |
| 2020/0047029 | A1 | 2/2020 | Bentley et al. | |
| 2020/0339693 | A1 | 10/2020 | Baret-Cormel et al. | |
| 2020/0399380 | A1 | 12/2020 | Boklage et al. | |
| 2020/0405851 | A1 | 12/2020 | Boyapati et al. | |
| 2021/0230719 | A1 | 7/2021 | Huang et al. | |
| 2021/0240369 | A1 | 8/2021 | Cain | |
| 2021/0301027 | A1 | 9/2021 | Sridhara Sundaram et al. | |
| 2022/0242959 | A1 | 8/2022 | Chen et al. | |
| 2023/0127528 | A1 | 4/2023 | Baret-Cormel et al. | |
| 2023/0174657 | A1 | 6/2023 | Albrecht et al. | |
| 2023/0193871 | A1 | 6/2023 | Ford et al. | |
| 2025/0333522 | A1 | 10/2025 | Boklage et al. | |

FOREIGN PATENT DOCUMENTS

| | | | |
|---|---|---|---|
| CN | 104105505 | A | 10/2014 |
| CN | 104903349 | A | 9/2015 |
| CN | 104998254 | A | 10/2015 |
| CN | 106413748 | A | 2/2017 |
| CN | 102869346 | A | 1/2023 |
| EA | 014226 | B1 | 10/2010 |
| EA | 014298 | B1 | 10/2010 |
| EP | 0628639 | A1 | 12/1994 |
| EP | 0409607 | B1 | 10/1996 |
| EP | 0783893 | A1 | 7/1997 |
| EP | 0800829 | A1 | 10/1997 |
| EP | 0811384 | A2 | 12/1997 |
| EP | 0923941 | A2 | 6/1999 |
| EP | 1 004 315 | | 5/2000 |
| EP | 1074268 | A1 | 2/2001 |
| EP | 1108435 | | 6/2001 |
| EP | 1314437 | A1 | 5/2003 |
| EP | 1327681 | | 7/2003 |
| EP | 1475100 | A1 | 11/2004 |
| EP | 1475101 | A1 | 11/2004 |
| EP | 0413908 | | 8/2005 |
| EP | 1810980 | A1 | 7/2007 |
| EP | 1334731 | | 2/2008 |
| EP | 2451438 | B1 | 2/2014 |
| EP | 2766039 | A1 | 8/2014 |
| EP | 3071230 | A1 | 9/2016 |
| EP | 3193934 | A1 | 7/2017 |
| EP | 3371224 | A1 | 9/2018 |
| EP | 3426295 | A1 | 1/2019 |
| EP | 3770173 | A1 | 1/2021 |
| EP | 3983071 | A1 | 4/2022 |
| FR | 2694767 | A1 | 2/1994 |
| JP | 2009-539349 | A | 11/2009 |
| JP | 2014-530226 | A | 11/2014 |
| JP | 61-22018 | B2 | 4/2017 |
| JP | 2017-137338 | A | 8/2017 |
| JP | 63-36171 | B2 | 5/2018 |
| JP | 2020-045351 | A | 3/2020 |
| KR | 10-2008-0011665 | A | 2/2008 |
| RU | 2358762 | C2 | 6/2009 |
| TW | 201141518 | A | 12/2011 |
| WO | WO 1992/016553 | A1 | 10/1992 |
| WO | WO 1992/019759 | A1 | 11/1992 |
| WO | WO 1994/006476 | A1 | 3/1994 |
| WO | WO 1995/009873 | A1 | 4/1995 |
| WO | WO 1996/011020 | A1 | 4/1996 |
| WO | WO 2002/100330 | A2 | 12/2002 |
| WO | WO 2003/009817 | A2 | 2/2003 |
| WO | WO 2004/039826 | A1 | 5/2004 |
| WO | WO 2004/091658 | A1 | 10/2004 |

(56) References Cited

FOREIGN PATENT DOCUMENTS

| | | | |
|---|---|---|---|
| WO | WO 2004/096273 | A1 | 11/2004 |
| WO | WO 2005/028514 | A1 | 3/2005 |
| WO | WO 2005/058365 | A1 | 6/2005 |
| WO | WO 2005/016280 | A2 | 2/2006 |
| WO | WO 2006/033702 | A2 | 3/2006 |
| WO | WO 2006/125229 | A2 | 11/2006 |
| WO | WO 2007/062040 | A1 | 5/2007 |
| WO | WO 2007/070750 | A1 | 6/2007 |
| WO | WO 2007/143168 | A2 | 12/2007 |
| WO | WO 2007/147001 | A2 | 12/2007 |
| WO | WO 2008/020079 | A1 | 2/2008 |
| WO | WO 2008/049897 | A1 | 5/2008 |
| WO | WO 2008/145142 | A1 | 12/2008 |
| WO | WO 2009/095489 | A2 | 8/2009 |
| WO | WO 2009/109584 | A1 | 9/2009 |
| WO | WO 2009/125825 | A1 | 10/2009 |
| WO | WO 2009/140348 | A2 | 11/2009 |
| WO | WO 2010/035769 | A1 | 4/2010 |
| WO | WO 2010/106812 | A1 | 9/2010 |
| WO | WO 2010/149771 | A1 | 12/2010 |
| WO | WO 2011/085158 | A2 | 7/2011 |
| WO | WO 2012/064627 | A2 | 5/2012 |
| WO | WO 2013/053751 | A1 | 4/2013 |
| WO | WO 2013/056751 | A1 | 4/2013 |
| WO | WO 2015/077582 | A1 | 5/2015 |
| WO | WO 2015/148790 | A1 | 10/2015 |
| WO | WO 2016/044343 | A1 | 3/2016 |
| WO | WO 2017/038986 | A1 | 3/2017 |
| WO | WO 2017/079443 | A1 | 5/2017 |
| WO | WO 2017/106312 | A1 | 6/2017 |
| WO | WO 2017/155990 | A1 | 9/2017 |
| WO | WO 2017/194779 | A1 | 11/2017 |
| WO | WO 2018/007442 | A1 | 1/2018 |
| WO | WO 2020/047029 | A1 | 3/2020 |
| WO | WO 2020/160465 | A1 | 8/2020 |
| WO | WO 2020/219960 | A1 | 10/2020 |
| WO | WO 2020/247461 | A1 | 12/2020 |
| WO | WO 2020/252214 | A1 | 12/2020 |
| WO | WO 2021/240436 | A1 | 12/2021 |

OTHER PUBLICATIONS

U.S. Appl. No. 13/183,014, filed May 22, 2012, Stevens et al.
"Nihon Naika Gakkai Zasshi", Japan Internal Medical Association Magazine, vol. 101, No. 10, pp. 2893-2898.
Advisory Action corresponding to U.S. Appl. No. 13/648,521, mailed Jul. 19, 2016.
Aletaha et al. (2010) "Rheumatoid Arthritis Classification Criteria, ACR classification," Arthritis & Rheumatism. 62 p. 2569-2581.
Amit et al., "Three-Dimensional Structure of an Antigen-Antibody Complex at 2.8 a Resolution" Science (Aug. 1986) 233:747-753.
An et al. (2010) "The addition of tocilizumab to DMARD therapy for rheumatoid arthritis: a meta-analysis of randomized controlled trials," 66(1):49-59.
Burmester et al. (Jul. 31, 2013) "A randomised, double-blind, parallel-group study of the safety and efficacy of subcutaneous tocilizumab versus intravenous tocilizumab in combination with traditional disease-modifying antirheumatic drugs in patients with moderate to severe rheumatoid arthritis (SUMMACTA study) ," Ann. Rheum. Dis. 73:69-74.
Center for Drug Evaluation and Research, Application No. 761037 (Year: 2016).
Chester (Jul. 24, 2017) E-mail: "<External> CAS Registry No. -RN1189541-98-7".
Chichasova (2010) "fletieume peama-rompuoro apTpwTa: Taiamyeume Bonpocbi B npaimike krimumumc-ra [Treatment pf rheumatoid arthritis: tactical issues in the practice of the clinician]," fleyaupin Bpati [The Attending Physician]. No. 7/10.—English machine translation only.
Choy et al., "Therapeutic benefit of blocking interleukin-6 activity with an anti-interleukin-6 receptor monoclonal antibody in rheumatoid arthritis: A randomized, double-blind, placebo-controlled, dose-escalation trial", Arthritis & Rheumatology, Dec. 2002, 46(12): 3143-3150.
ClinicalTrials.gov archive NCT01061736 (2010), p. 1-2.
Daugherty et al., "Formulation and delivery issues for monoclonal antibody therapeutics," Adv. Drug Delivery Reviews, 58:686-706, (2006).
Emery et al. (2008)., Ann. Rheum. Dis., vol. 67, pp. 1516-1523.
Fleischmann et al. "Comparable Efficacy with Sarilumab Plus Methotrexate in Biologic-Experienced and Biologic-Naive Patients with Moderate-to-Severe Rheumatoid Arthritis from a Phase 3, Randomized, Double-Blind, Placebo-Controlled, International Study." Arthritis & Rheumatology. vol. 66. 111 River St, Hoboken 07030-5774, NJ USA: Wiley-Blackwell, 2014.
Gandek et al. (2004) "Psychometric evaluation of the SF-36 health survey in Medicare managed care," Health Care inanc Rev. 25(4):5-25.
Genentech (2014) Actemra Subcutaneous Dosing & Administration Pocket Guide. pp. 1-40.
Hennigan et al., "Interleukin-6 inhibitors in the treatment of rheumatoid arthritis", Therapeutic and Clinical Risk Management , 4(4), 767-775. (Year: 2008).
Hirata et al., "Characterization of IL-6 Receptor Expression By Monoclonal and Polyclonal Antibodies" J. Immunol. (1989) 143(9):2900-2906.
International Nonproprietary Names for Pharmaceutical Substances (INN) WHO Drug Information, vol. 25, No. 4, 2011; 53 pages.
International Search Report with Written Opinion corresponding to International Patent Application No. PCT/ US2015/050291, mailed Dec. 1, 2015.
International Search Report with Written Opinion corresponding to International Patent Application No. PCT/ JS2014/066856, mailed Apr. 2, 2015.
International Search Report with Written Opinion corresponding to International Patent Application No. PCT/ EP2012/070052, mailed Dec. 7, 2012.
Kivitz (Nov. 2014) "Subcutaneous Tocilizumab vs Placebo in Combination with Disease Modifying Antirheumatic Drugs in Patients with Rheumatoid Arthritis," Arthritis Care Res. (Hoboken). 66(11):1653-1661.
Langer (1990) "New Methods of Drug Delivery," Science. 249:1527-1533.
Lederman et al. "A Single Amino Acid Substitution in a Common African Allele of the CD4 Molecule Ablates Binding of the Monoclonal Antibody, OKT4" Molecular Immunology (1991) 28(11):1171-1181.
Li et al. "Temporal associations between interleukin 22 and the extracellular domains of IL-22R and IL-10R2" International Immunology (2004) 4:693-708.
Meehan et al. (1996) "A microinfusor device for the delivery of therapeutic levels of peptides and macromolecules," Journal of Controlled Release. 46:107-116.
Mihara et al., 2005, Tocilizumab inhibits signal transduction mediated by both MIL-6R and sIL-6R, but not by the receptors of other members of IL-6 cyotkine family, International Immunopharmacology 5:1731-1740.
Niishimoto et al. (2009) "Study of active controlled tocilizumab monotherapy for rheumatoid arthritis patients with an nadequate response to methotrexate (SATORI): significant reduction in disease activity and serum vascular andothelial growth factor by IL-6 receptor inhibition therapy," Modem Rheumatology. 19(1):12-19.
Office Action corresponding to U.S. Appl. No. 13/648,521, mailed Jun. 26, 2015.
Office Action corresponding to U.S. Appl. No. 13/648,521, mailed Mar. 10, 2014.
Office Action corresponding to U.S. Appl. No. 13/648,521, mailed Oct. 18, 2013.
Office Action corresponding to U.S. Appl. No. 13/648,521, mailed Feb. 11, 2016.
Office Action corresponding to U.S. Appl. No. 13/648,521, mailed Mar. 19, 2015.
Office Action corresponding to U.S. Appl. No. 13/648,521, mailed Jul. 3, 2014.

(56) References Cited

OTHER PUBLICATIONS

Panka et al., "Variable Region Framework Differences Result in Decreased or Increased Affinity of Variant Anti-Digoxin Antibodies" Proc. Natl. Acad. Sci. USA (May 1988) 85:3080-3084.
Patro et al., "Protein formulation and fill-finish operations," Biotechnol Annu Rev, 8:55-84, (2002). Abstract only.
Paul-Pletzer, 2006, Tocilizumab: Blockade of interleukin-6 signaling pathway as a therapeautic strategy for inflammatory disorders, Drugs of Today 42(9):559-576.
Powchik (2010),Regeneron Investor Day, p. 1-19.
Powell et al. (1998) "Compendium of Excipients for Parenteral Formulations," PDA Journal of Pharmaceutical Science and Technology. 52:238-311.
Presta, Leonard G., "Engineering of therapeutic antibodies to minimize immunogenicity and optimize function" Advanced Drug Delivery Reviews (2006) 58:640-656.
Radin et al. (Jan. 1, 2010) "Safety and effects on markers of inflammation of subcutaneously administered regn88/ sar153191 (regn88), an interleukin-6 receptor inhibitor, in patients with rheumatoid arthritis: findings from phase 1 studies," [Abstract] Annals of the Rheumatic Diseases. 69(Suppl. 3):99.
Radin et al. (Nov. 2010) "REGN88/SAR153191, a Fully-Human Interleukin-6 Receptor Monoclonal Antibody, Reduces, Acute Phase Reactants in Patients with Rheumatoid Arthritis: Preliminary Observations from Phase 1, Studies," [Abstract] Arthritis. Rheum. 62(Suppl. 10):1121.
Reddy et al., "Elimination of Fc Receptor-Dependent Effector Functions of a Modified IgG4 Monoclonal Antibody to Human CD4," Journal of Immunology, 164:1925-1933 (2000).
Regeneron Pharmaceuticals, Inc., "Sanofi And Regeneron Announce Patient Enrollment In Two Phase 3 Trials With Sarilumab In Rheumatoid Arthritis (RA)", Online Publication, May 15, 2013 at 1:00 AM EDT.
Regeneron Pharmaceuticals (Jul. 12, 2011) "Sanofi and Regeneron Report Positive Phase 2b Trial Results with Sarilumab in Rheumatoid Arthritis," Acquire Media. Accessible on the Internet at URL: http://web.archive.org/web/20110818152737/http://investorregeneron.com/releasedetail.cfm?ReleaseID=590869. [Last Accessed May 4, 2016].
Regeneron Pharmaceuticals (Jul. 12, 2011) "Evaluation of Sarilumab (SAR153191/REGN88) on Top of Methotrexate in Rheumatoid Arthritis Patients (RA-Mobility)", Retrieved from the internet from URL: <<https://clinicaltrials.gov/ct2/results?term=SAR+153191=mobility>>.
Regeneron Pharmaceuticals, Inc. (Jun. 12, 2014) "Sanofi and Regeneron announce new, detailed data from positive Sarilumab phase 3 rheumatoid arthritis trial at EULAR," Press Release. Acquire Media.
Regeneron Pharmaceuticals, Inc. (Nov. 22, 2013) "Sanofi and Regeneron report positive results with Sarilumab in first phase 3 rheumatoid arthritis registration trial," Press Release. Acquire Media.
Reichert (Jan. 1, 2011) "Antibody-based therapeutics to watch in 2011," MAbs. 3:76-99.
Restriction Requirement corresponding to U.S. Appl. No. 13/648,521, mailed Jun. 10, 2013.
Rudikoff et al., "Single Amino Acid Substitution Altering Antigen-Binding Specificity" Proc. Natl. Acad. Sci. USA (Mar. 1982) 79:1979-1983.
Sanofi (Feb. 2, 2010) "Evaluation of SARI 53191(REGN88) (Sarilumab) on Top of Methotrexate in Rheumatoid Arthritis Patients (RA-Mobility)," ClinicalTrials.gov. http://clinicaltrials.gov/show/NCT01061736 [Last Accessed on Jan. 21, 2015].
Sanofi (Oct. 7, 2010) "Effect of SARI 53191 (REGN88) With Methotrexate in Patients With Active Rheumatoid Arthritis Who Failed INF-a Blockers," ClinicalTrials.gov http://clinicaltrials.gov/show/NCT01217814 [Last Accessed on Jul. 16, 2014].
Sanofi (Nov. 7, 2013) View of NCT01061736 on Nov. 7, 2013 ClinicalTrials.gov. Accessible on the Internet at URL: https://clinicaltrials.gov/archive/NCT01061736/2013_11_07. [Last Accessed Aug. 30, 3016].
Sanofi (Sep. 27, 2011) View of NCT01217814 on Sep. 27, 2011 ClinicalTrials.gov. Accessible on the Internet at JRL: https://clinicaltrials.gov/archive/NCT01217814/2011_09_27. [Last Accessed Aug. 30, 3016].
Sanofi and Regeneron (May 21, 2015) "Sanofi and Regeneron announce positive topline results from phase 3 studies with sarilumab in patients with rheumatoid arthritis," Press Release. Sanofi. Accessible on the Internet at URL: http://mediaroom.sanofi.com/sanoThand-regeneron-announce-positive-topline-results-from-phase-3-studies-with-sarilumab-in-patients-with-rheumatoid-arthritis-2. [Last Accessed Aug. 30, 2016].
Sanofi and Regeneron (Nov. 8, 2015) "Regeneron and Sanofi Present Results from Pivotal Phase 3 Study of Sarilumab at American College of Rheumatology Annual Meeting," Press Release. Regeneron Pharmaceuticals, Inc. Accessible on the Internet at URL: http://investorregeneron.com/releasedetail.cfm?releaseid=941387. [Last Accessed Aug. 30, 2016].
Shields et al., "Lack of Fucose on Human IgG1 N-Linked Oligosaccharide Improves Binding to Human Fc gamma RIII and Antibody-dependent Cellular Toxicity," Journal of Biological Chemistry, 277(30):26733-26740 (2002).
Smolen et al. (2008) "Effect of interleukin-6 receptor inhibition wuth tocilizumab in patients with rheumatoid arthritic (Option study): a double blind, placebo-controlled, randomised trial," Lancet. 371:987-997.
Taylor (2010) Pharmacology of TNF blockade in rheumatoid arthritis and other chronic inflammatory diseases // 3urr. Opin. Pharmacol. 10(3):308-315.
The Chemical Abstracts Service (CAS) entry for registration No. 1189541-98-7.
Uchiyama et al., "Tocilizumab, a Humanized Anti-interleukin-6 Receptor Antibody, Ameliorates Joing Swelling in Established Monkey Collagen-Induced Arthritis" Biol. Pharm. Bull. (2008) 31(6):1159-1163.
United States Adopted Names Council (Date Publicly Available Unclear) "Statement on a nonproprietary name adopted by the USAN council: Sarilumab," CAS Registry No. 1189541-98-7.
Vasanthi, et al. (Dec. 2007) "Role of Tumor Necrosis Factor-Alpha in Rheumatoid Arthritis: A Review", APLAR Journal of Rheumatology, vol. 10, No. 4, pp. 270-274.
Wang et al., "Minireview: Antibody Structure, Instability, and Formulation," Journal of Pharmaceutical Sciences, 96(1):1-26, (2007).
Wang, "Instability, stabilization, and formulation of liquid protein pharmaceuticals," Int'l J. Pharmaceutics, 185(2):129-188, (1999).
Whalley et al. (1997) "Quality of life in rheumatoid arthritis," Br. J. Rheumatol. 36:884-888.
Wu et al. (1987) "Receptor-mediated in Vitro Gene Transformation by a soluble DNA Carrier System," The Journal of Biological Chemistry. 262:4429-4432.
Redlich et al., "Inflammatory bone loss: pathogenesis and therapeutic intervention", Nat rev Drug Discov., Mar. 2012, 11(3): 234-250.
U.S. Appl. No. 17/133,870, filed Dec. 24, 2020, Xiaohong Huang.
U.S. Appl. No. 14/350,973 2014/0302053 U.S. Pat. No. 10,927,435, filed Apr. 10, 2014 Oct. 9, 2014 Feb. 23, 2021, Xiaohong Huang.
U.S. Appl. No. 15/034,531 2016/0280782, filed May 4, 2016 Sep. 29, 2016, Xiaohong Huang.
U.S. Appl. No. 15/910,733 2018/0296670, filed Mar. 2, 2018 Oct. 18, 2018, Martine Jasson.
U.S. Appl. No. 13/648,521 2013/0149310 U.S. Pat. No. 9,943,594, filed Oct. 10, 2012 Jun. 13, 2013 Apr. 17, 2018, Martine Jasson.
"Highlights of Prescribing Information" for KEVZARA (sarilumab), Reference ID: 4101405—Accessdata.fda.gov, May 2017.
Actemra Prescribing Information Genentech. Actemra (tocilizumab): Full Prescribing Information. 2017 Retrieved from: <<https://www.accessdata.fda.gov/drugsatfda_docs/label/2017/125276s114lbl.pdf>>.
Adan, et al., "Tocilizumab Treatment For Refractory Uveitis-Related Cystoid Macular Edema", Graefe's Archive for Clinical and Experimental Ophthalmology, vol. 251, No. 11, pp. 2627-2632, Jul. 27, 2013.

(56) References Cited

OTHER PUBLICATIONS

Adlan, et al., Autonomic Function and Rheumatoid Arthritis—A Systematic Review, Seminars in Arthritis and Rheumatism, vol. 44, No. 3, pp. 283-304, 2014.

Advisory Action received for U.S. Appl. No. 13/648,521, mailed on Jul. 19, 2016, 3 Pages.

Alekseeva, "Juvenile Idiopathic Arthritis: Clinical Picture, Diagnosis, Treatment," Current Pediatrics, 2015, 14(1): 78-94, Etiology and Pathogenesis, p. 78; Treatment of Polyarticular (RF−, RF+) JIA, p. 84; and Treatment, p. 92, English Abstract included.

Andersson M. et al., "SAT0116 Prevalence of unacceptable pain in patients with long-standing RA", Annals of the Rheumatic Diseases, 2017, 76: p. 812-813.

Arevalo, "Tocilizumab Shows Promise For Refractory Uveitis-Related Macular Edema", URL:https://www.aao.org/editors-choice/tocilizumab-shows-promise-refractory-uveitISRWOelate, Nov. 25, 2014.

Atzeni et al., "Il-6 Involvement in pain, fatigue and mood disorders in rheumatoid arthritis and the effects of Il-6 inhibitor sarilumab", Pharmacological Research, 2019, 149: 1-8.

Barry, et al., "Pharmacotherapy for Uveitis: Current Management and Emerging Therapy", Clinical Ophthalmology, vol. 8, pp. 1891-1911, Sep. 1, 2014.

Biswas, et al., Prevalence, Types, Clinical Associations, and Determinants of Peripheral Neuropathy in Rheumatoid Patients, Annals of Indian Academy of Neurology, vol. 14, No. 3, pp. 194-197, 2011.

Boyapati, et al., "Sarilumab Plus Methotrexate Suppresses Circulating Biomarkers of Bone Resorption and Synovial Damage in Patients with Rheumatoid Arthritis and Inadequate Response to Methotrexate: A Biomarker Study of Mobility", Arthritis Research & Therapy, vol. 18, Article No. 225, pp. 1-12, Dec. 1, 2016.

Boyden et al., Non-inflammatory Causes of Pain in Patients with Rheumatoid Arthritis, Curr Rheumatol Rep., 2016, 18: 30.1.

Brenn, et al., Sensitization of Unmyelinated Sensory Fibers of the Joint Nerve to Mechanical Stimuli by Interleukin-6 in the Rat: an Inflammatory Mechanism of Joint Pain, Arthritis & Rheumatology, vol. 56, No. 1, pp. 351-359, Jan. 2007.

Bresnick, "Diabetic Macular Edema—A Review", Ophthalmology, vol. 93, No. 7, pp. 989-997, Jul. 1986.

Burmester et al., "Efficacy and safety of subcutaneous tocilizumab versus intravenous tocilizumab in combination with traditional DMARDs in patients with RA at week 97 (SUMMACTA)", Annals of the Rheumatic Diseases, Jun. 8, 2015, vol. 75, No. 1, pp. 68-74.

Burmester et al., "Efficacy and safety of sarilumab monotherapy versus adalimumab monotherapy for the treatment of patients with active rheumatoid arthritis (MONARCH): a randomised, double-blind, parallel-group phase III trial", Ann Rheum Dis., 2017, 76(5): 840-847.

Burmester et al., "Rheumatoid Arthritis—Sarilumab more effective than adalimumab", Nature Reviews, Rheumatology, Research Highlights, Published online Dec. 8, 2016.

Burmester et al., "Safety and efficacy of switching from adalimumab to sarilumab in patients with rheumatoid arthritis in the ongoing MONARCH open-label extention", RMD Open, Rheumatic and Musculoskeletal Diseases, 2019, 5: e001017.

Burmester, et al. Unique Changes in Hemoglobin with Sarilumab Versus Adalimumab are Independent of Better Disease Control in Patients with Rheumatoid Arthritis (RA) Arthritis & Rheumatology, 2018 vol. 70, Supplement 10, Abstract 1528.

Bykerk et al., "Impact of Sarilumab on Unacceptable Pain and Inflammation Control in Moderately-to-Severely Active Rheumatoid Arthritis (RA) Patients in 3 Phase 3 Studies", Arthritis & Rheumatology (Hoboken), Oct. 1, 2019, 71(S10): Abstract No. 1393.

Bykerk et al., "Impact of sarilumab on unacceptable pain and inflammation control in moderately-to-severely active rheumatoid arthritis (RA) patients in 3 Phase 3 studies", Rheumatology, Apr. 20, 2020, 59(2): EP25.

Bykerk et al., "Impact of Sarilumab on Unacceptable Pain and Inflammation Control in Moderately-to-Severely Active Rheumatoid Arthritis Patients in 3 Phase 3 Studies", Sep. 11, 2020, retrieved from url: https://pheedloop.s3.amazonaws.com/media/events/EVEVLUEFMPIXU/files/822199_Bykerk-Vivian-RA-Unacceptable%20Pain.pdf.

Calabrese, et al., "IL-6 Biology: Implications for Clinical Targeting in Rheumatic Disease", Nature Reviews Rheumatology, vol. 10, No. 12, pp. 720-727, Dec. 2014.

Cao, et al., "Pharmacological Blockade Of Interleukin 6 Receptor (IL-6R) Inhibits The Development Of Ocular Inflammation In The Murine Model Of Experimental Autoimmune Uveitis (EAU)", Investigative Ophthalmology & Visual Science, vol. 54, Issued 15, p. 5193, Jun. 2013.

Cazzola et al., Physiopathology of Pain in Rheumatology, Reumatismo, vol. 66, No. 1, pp. 4-13, 2014.

Challa, et al., Patient-provider Discordance Between Global Assessments of Disease Activity in Rheumatoid Arthritis: a Comprehensive Clinical Evaluation, Arthritis Research & Therapy, vol. 19, No. 212, pp. 1-14, 2017.

Cheung, et al., "2-093 Comparative Effectiveness of Biologic Dmards and Jak Inhibitors in Patients With an Inadequate Response to TNF Inhibitors: a Network Meta-analysis", International Journal of Rheumatic Diseases, Retrieved From url: <<https://onlinelibrary.wiley.com/doi/10.1111/1756-185X.13545>>.

Choy et al., "Indirect Treatment Comparison of the Efficacy and Safety of Sarilumab Monotherapy in Rheumatoid Arthritis Patients with Inadequate Response to Conventional Disease-Modifying Antirheumatic Drugs", Mar. 12, 2019, 36(4): 817-827.

Choy, "Understanding the Dynamics: Pathways Involved in the Pathogenesis of Rheumatoid Arthritis", Rheumatology, vol. 51, Supplement 5, pp. v3-v11, Jul. 1, 2012.

Choy, et al., "Cardiovascular Risk in Rheumatoid Arthritis: Recent Advances in the Understanding of the Pivotal Role of Inflammation", Risk Predictors and the Impact of Treatment Rheumatology, vol. 53, pp. 2143-2154, Dec. 1, 2014.

Choy, et al., "Neuroendocrine and Neurophysiological Effects of Interleukin 6 in Rheumatoid Arthritis", Rheumatology, vol. 57, pp. 1885-1895, Nov. 1, 2018.

ClinicalTrials.gov (Oct. 22, 2019) "Efficacy and Safety of GSK3196165 (Otilimab) Versus Placebo and Sarilumab in Participants With Moderately to Severely Active Rheumatoid Arthritis Who Have an Inadequate Response to Biological Disease-modifying Antirheumatic Drug (DMARDs) and/or Janus Kinase (JAK) Inhibitors (contRAst 3)", ClinicalTrials.gov Identifier: NCT04134728.

ClinicalTrials.gov, (Apr. 13, 2015) "Phase II Study to Analyze Sarilumab in Non-Infectious Uveitis", ClinicalTrials.gov Identifier: NCT01900431.

ClinicalTrials.gov, (Dec. 13, 2016) "A Repeated Dose-finding Study of Sarilumab in Children and Adolescents With Systemic Juvenile Idiopathic Arthritis (SKYPS)", ClinicalTrials.gov Identifier: NCT02991469.

ClinicalTrials.gov, (Feb. 26, 2015) "A Study Assessing the Safety and Efficacy of Sarilumab Added to Non-MTX DMARDs or as Monotherapy in Japanese Patients With Active Rheumatoid Arthritis", ClinicalTrials.gov Identifier: NCT02373202.

ClinicalTrials.gov, (Jan. 7, 2015) "Efficacy and Safety of Sarilumab and Adalimumab Monotherapy in Patients With Rheumatoid Arthritis (SARIL-RA-MONARCH)", ClinicalTrials.gov Identifier: NCT02332590.

ClinicalTrials.gov, (Jun. 8, 2015) "Phase II Study to Analyze Sarilumab in Non-Infectious Uveitis", ClinicalTrials.gov Identifier: NCT01900431.

ClinicalTrials.gov, (May 18, 2016) "An Open-label, Ascending, Repeated Dose-finding Study of Sarilumab in Children and Adolescents With Polyarticular-course Juvenile Idiopathic Arthritis (pcJIA) (SKYPP)", ClinicalTrials.gov Identifier: NCT02776735.

ClinicalTrials.gov, (Oct. 7, 2010), "Evaluation of Sarilumab (SAR153191/REGN88) on Top of Methotrexate in Rheumatoid Arthritis Patients (RA-MOBILITY)", ClinicalTrials.gov Identifier: NCT01061736.

ClinicalTrials.gov, (Oct. 18, 2012.) "To Evaluate The Effect Of SAR153191 (REGN88) Added To Other RA Drugs In Patients With

(56) References Cited

OTHER PUBLICATIONS

RA Who Are Not Responding To Or Intolerant Of Anti-TNF Therapy (SARIL-RA-TARGET)", ClinicalTrials.gov Identifier: NCT01709578.
ClinicalTrials.gov, (Oct. 29, 2012) "Study of the Safety, Tolerability, and Bioactivity of Tocilizumab on Patients with Non-infectious UVEITIS, The STOP-UVEITIS Study", ClinicalTrials.gov Identifier: NCT01717170.
Corevitas, Rheumatoid Arthritis Registry, Available from: https://www.corevitas.com/registry/rheumatoid-arthritis, Accessed on Aug. 26, 2022.
Cronstein, "Low-Dose Methotrexate: A Mainstay in the Treatment of Rheumatoid Arthritis", Pharmacological Reviews, Jun. 2005, 57(2): 163-172.
Curtis et al., "Determining the minimally important difference in the clinical disease activity index for improvement and worsening in early rheumatoid arthritis patients", Arthritis Care Res (Hoboken), 2015, 67(10): 1345-1353.
Curtis, et al. Reanalysis of the Multi-Biomarker Disease Activity Score for Assessing Disease Activity in the Abatacept Versus Adalimumab Comparison in Biologic-Naive Rheumatoid Arthritis Subjects with Background Methotrexate Study: Comment on the Article by Fleischmann, Arthritis & Rheumatology, Apr. 2017, vol. 69, No. 4, pp. 863-872.
Dasgupta et al., "Sarilumab In Patients With Relapsing Polymyalgia Rheumatica: A Phase 3, Multicenter, Randomized, Double Blind, Placebo Controlled Trial (Saphyr)", Annals Of The Rheumatic Diseases, EULAR European Congress Of Rheumatology (EULAR); Copenhagen, Denmark; Jun. 1-4, 2022, British Medical Association, GB, May 31, 2022, 81(Suppl. 1): 210-211.
Davis, et al., "Scale For Photographic Grading Of Vitreous Haze In Uveitis", American Journal of Ophthalmology, vol. 150, No. 5, pp. 637-641, Nov. 2010.
De Benedetti et al., "FRI0549—Sarilumab, a Human Monoclonal Antibody to the Interleukin-6 (IL-6) Receptor, In Polyarticular-Course Juvenile Idiopathic Arthritis (pcJIA): A 12-Week Multinational Open-Label Dose-Finding Study", Annals of the Rheumatic Diseases, Jun. 2019, 78(Suppl 2): 969-970.
De Benedetti et al., "Sarilumab, a Human Monoclonal Antibody to the Interleukin- 6 Receptor, in Polyarticular-course Juvenile Idiopathic Arthritis: A 12-week, Multinational, Open-label, Dose-Finding Study", Meeting: 2019 ACR/ARP Annual Meeting, American College of Rheumatology, Abstract No. 2710, Nov. 12, 2019.
De Haas, et al., Rheumatoid Arthritis, Typus Robustus, Annals of the Rheumatic Diseases, vol. 32, No. 1, pp. 91-92, 1973.
Deane, et al., Preclinical Rheumatoid Arthritis: Identification, Evaluation, and Future Directions for Investigation, Rheumatic Disease Clinics of North America, vol. 36, No. 2, pp. 213-241, 2010.
Dennis Jr., et al., "Synovial Phenotypes in Rheumatoid Arthritis Correlate with Response to Biologic Therapeutics", Arthritis Research & Therapy, vol. 16, Article No. R90, pp. 1-18, Apr. 2014.
Dhillon, Intravenous Tocilizumab: A Review of Its Use in Adults with Rheumatoid Arthritis, BioDrugs, vol. 28, pp. 75-106, 2014.
Durán, et al., The Effect on Treatment Response of Fibromyalgic Symptoms in Early Rheumatoid Arthritis Patients: Results From the Espoir Cohort, Rheumatology, vol. 54, No. 12, pp. 2166-2170, 2015.
Durrani, et al., "Degree, Duration, And Causes Of Visual Loss In Uveitis", British Journal of Ophthalmology, vol. 88, No. 9, pp. 1159-1162, Sep. 2004.
Eberhard A., et al., "AB0285 Predictors of unacceptable pain and unacceptable pain with low inflammation, in early rheumatoid arthritis", Annals of the Rheumatic Diseases, pp. 1600, 2019.
Elixhauser, et al., Comorbidity Measures for Use with Administrative Data, Medical Care, vol. 36, No. 1, pp. 8-27, Jan. 1988.
European Medicines Agency, Committee for Medicinal Products for Human Use (CHMP), Assessment Report, Apr. 21, 2017, EMA/292840/2017, retrieved from url: https://www.ema.europa.eu/en/documents/assessment-report/kevzara-epar-public-assessment-report_en.pdf.
Extended European Search Report received for European Patent Application No. 20167644.2, mailed on Oct. 21, 2020, 8 Pages.
Feist, et al., "Abstract 0832 Prosara—A Prospective, Multicenter, Noninterventional Study to Evaluate the Safety and Effectiveness of Sarilumab for the Treatment of Active Rheumatoid Arthritis in Regular Care in Germany", ACR Convergence, Nov. 5-9, 2020, Meeting Abstracts.
Feist, et al., "THU0165 Prosara—a Prospective, Multicenter, Non-interventional Study to Evaluate the Safety and Effectiveness of Sarilumab for the Treatment of Active Rheumatoid Arthritis in Regular Care in Germany", Annals of the Rheumaic Diseases, Scientific Abstracts, Jun. 2020.
Final Office Action received for U.S. Appl. No. 13/648,521, mailed on Feb. 11, 2016, 13 Pages.
Final Office Action received for U.S. Appl. No. 13/648,521, mailed on Mar. 10, 2014, 9 Pages.
Fleischmann et al., "Efficacy and Safety of Sarilumab in Connection with CsDMARDs in Patients with Active Rheumatoid Arthritis Who Were Inadequate Responders or Intolerant of Anti-TNF-alpha Therapy: Results from a Phase 3 Study", ACR Abstract 970; Nov. 8, 2015.
Fleischmann, et al., "Estimating Disease Activity using Multi-Biomarker Disease Activity Scores in Rheumatoid Arthritis Patients Treated with Abatacept or Adalimumab", Arthritis & Rheumatology, vol. 68, No. 9, pp. 2083-2089, Sep. 2016.
Fleischmann, et al., "Sarilumab and Nonbiologic Disease-Modifying Antirheumatic Drugs in Patients with Active Rheumatoid Arthritis and Inadequate Response or Intolerance to Tumor Necrosis Factor Inhibitors", Arthritis & Rheumatology, vol. 69, No. 2, pp. 277-290, Feb. 2017.
Flodin, et al., Intrinsic Brain Connectivity in Chronic Pain: A Resting-State fMRI Study in Patients with Rheumatoid Arthritis, Frontiers in Human Neuroscience, vol. 10, No. 107, pp. 1-8, Mar. 2016.
Fortin, et al., "Glossary of Selected Terms—A Systematic Review of Intravitreal Bevacizumab for the Treatment of Diabetic Macular Edema" NCBI Bookshelf, XP055753991, Retrieved from: <<https://www.ncbi.nlm.nih.gov/books/NBK169468/>>, 2 Pages, May 1, 2012.
Fragiadaki et al., Sleep Disturbances and Interleukin 6 Receptor Inhibition in Rheumatoid Arthritis, J Rheumatol., 2012, 39: 60-62.
Fransen et al., "The Disease Activity Score and the EULAR response criteria", Clinical and Experimental Rheumatology, Aug. 31, 2005, 23(5 Suppl 39): S93-99).
Gabay et al., "Tocilizumab monotherapy versus adalimumab monotherapy for treatment of rheumatoid arthritis (ADACTA): a randomised, double-blind, controlled phase 4 trial", Lancet, 2013, 381(9877): 1541-1550.
Gabay, et al., "Comparison of Lipid and Lipid-Associated Cardiovascular Risk Marker Changes After Treatment With Tocilizumab or Adalimumab in Patients with Rheumatoid Arthritis", Annals of the Rheumatic Diseases, vol. 75, pp. 1806-1812, Oct. 1, 2016.
Gabay, et al., "Effect of Sarilumab on Circulating Biomarkers of Bone and Joint Destruction in Patients with Rheumatoid Arthritis with Inadequate Response to Methotrexate", Arthritis & Rheumatology, vol. 68, Supplement 10, p. 3091, Oct. 2016.
Gabay, et al., "Identification of Sarilumab Pharmacodynamic and Predictive Markers in Patients with Inadequate Response to TNF Inhibition: A Biomarker Substudy of the Phase 3 Target Study", Rheumatic & Musculoskeletal Diseases Open, vol. 4, e000607, pp. 1-11, Mar. 1, 2018.
Garces, et al., Comparison of Dose Escalation and Costs of Dose Escalation Between Patients With Rheumatoid Arthritis Initiating Biologic Treatment With Etanercept, Adalimumab, or Infliximab, Value in Health, vol. 19, No. 3, pp. A229-A230, 2016.
Gavrilă, et al., "Biomarkers in Rheumatoid Arthritis, What Is New?", Journal of Medicine and Life, vol. 9, Issue 2, pp. 144-148, Apr.-Jun. 2016.
Genbank, "*H. sapiens* Serum Amyloid A Protein mRNA", Complete cds, Genbank Accession No. M81349.1, Retrieved from: <<https://www.ncbi.nlm.nih.gov/nuccore/M81349.1>>, 1 Page.

(56) References Cited

OTHER PUBLICATIONS

Genbank, "*Homo sapiens* C-Reactive Protein (CRP)", RefSeqGene on Chromosome 1, Genbank Accession No. NG_013007.1, Retrieved from: <<https://www.ncbi.nlm.nih.gov/nuccore/NG_013007.1>>, pp. 1-4.

Genbank, "*Homo sapiens* C-X-C Motif Chemokine Ligand 13 (CXCL13)", Transcript Variant 1, mRNA, Genbank Accession No. NM_006419.2, Retrieved from: <<https://www.ncbi.nlm.nih.gov/nuccore/NM_006419.2>>, pp. 1-4., Jul. 31, 2008.

Genbank, "*Homo sapiens* Intercellular Adhesion Molecule 1 (ICAM1)", mRNA, Genbank Accession No. NM_000201.3, Retrieved from: <<https://www.ncbi.nlm.nih.gov/nuccore/NM_000201.3>>, pp. 1-5., Nov. 23, 2018.

Genbank, *Homo sapiens* Matrix Metallopeptidase 3 (MMP3), mRNA, Genbank Accession No. NM_002422.5, Retrieved from: <<https://www.ncbi.nlm.nih.gov/nuccore/NM_002422.5>>, pp. 1-4, Nov. 22, 2018.

Genentech (Apr. 11, 2019) ACTEMRA® (tocilizumab) injection, for intravenous or subcutaneous use.

Genovese, et al., "293 A Phase 3 Clinical Program of Three, Randomized, Double-blind, Placebo- and Comparator-controlled Studies to Assess the Efficacy and Safety of Otilimab in RA: Study Design and Methodology", Journal of Clinical Rheumatology, Retrieved From url:<<https://journals.lww.com/jclinrheum/Fulltext/2020/04001/22nd_PANLAR_Congress_Miami,_FL,_August_12_15_2020.1.aspx>>.

Genovese, et al., "Efficacy and Safety of Sarilumab in Combination With csDMARDs or as Monotherapy in Subpopulations of Patients With Moderately to Severely Active Rheumatoid Arthritis in Three Phase III Randomized", Controlled Studies, Arthritis Research & Therapy, vol. 22, No. 1, pp. 1-17, 2020.

Genovese, et al., "Long-term Safety and Efficacy of Sarilumab Plus Methotrexate on Disease Activity, Physical Function and Radiographic Progression: 5 Years of Sarilumab Plus Methotrexate Treatment", Rheumatic & Musculoskeletal Disease, vol. 5, No. 2, pp. 1-10, 2019.

Genovese, et al., "Sarilumab Plus Methotrexate in Patients with Active Rheumatoid Arthritis and Inadequate Response to Methotrexate: Results of a Phase III Study", Arthritis & Rheumatology, vol. 67, No. 6, pp. 1424-1437, Jun. 1, 2015.

Genovese, et al., "Switching Between the JAK1-selective Inhibitor Upadacitinib and Adalimumab Following Initial Non-response: Clinical and Functional Outcomes Among Rheumatoid Arthritis Patients", Oral Presentations, Jun. 12, 2019, RA therapy—JAK inhibitors and beyond.

Genovese, et al., Interleukin-6 Receptor Inhibition With Tocilizumab Reduces Disease Activity in Rheumatoid Arthritis With Inadequate Response to Disease-modifying Antirheumatic Drugs: the Tocilizumab in Combination With Traditional Disease-modifying Antirheumatic Drug Ther, Arthritis & Rheumatism: Official Journal of the American College of Rheumatology, vol. 58, No. 10, pp. 2968-2980, Sep. 29, 2008.

Georgy, et al., A Clinical Study to Assess the Pharmacokinetics and Pharmacodynamics of Tocilizumab After a Single Dose Administration by Subcutaneous and Intra Venous Routes to Healthy Subjects, Clinical Pharmacology & Therapeutics, vol. 87, No. S1, p. S60, Feb. 15, 2010.

Gordon, et al., "pANCA Antibodies In Patients With Anterior Uveitis: Identification Of A Marker Antibody Usually Associated With Ulcerative Colitis", Journal of Clinical Immunology, vol. 18, No. 4, pp. 264-271, Jul. 1998.

Hammer, et al., Major Reduction of Ultrasound Detected Synovitis during Subcutaneous Tocilizumab Treatment; Results from a Multicenter 24 Weeks Study of Patients with Rheumatoid Arthritis, Arthritis & Rheumatology, vol. 70, No. S9, pp. 1537-1538, 2018.

HAQ—Health Assessment Questionnaire, Scleroderma Study Conference, English Translation, Retrieved from URL: <<http://derma.w3.kanazawa- .ac.jp/SSc/pamphret/HAQ.html >>,6 Pages (4 Pages of English Translation & 2 Pages of Official Copy), Jul. 30, 2019.

Hashimoto et al., "Increase of Hemoglobin Levels by Anti-IL-6 Receptor Antibody (Tocilizumab) in Rheumatoid Arthritis", PLoS One, May 30, 2014, vol. 9, No. 5, pp. e98202: 1-7.

Heidari et al., "Rheumatoid Arthritis: Early Diagnosis and Outcomes", Caspian Journ Intern Med., Winter 2011, 2(1): 161-170.

Huizinga, et al., "Sarilumab, A Fully Human Monoclonal Antibody Against IL-6Rα in Patients with Rheumatoid Arthritis and an Inadequate Response to Methotrexate: Efficacy and Safety Results from the Randomised SARIL-RA-MOBILITY Part A Trial", Annals of the Rheumatic Diseases, vol. 73, No. 9, pp. 1626-1634, Sep. 1, 2014.

HUMIRA® (Adalimumab) Injection, for Subcutaneous Use, Highlights of Prescribing Information, United States Food and Drug Administration, Retrieved from: <<https://www.accessdata.fda.gov/drugsatfda_docs/label/2018/125057s410lbl.pdf>>, 104 Pages, Dec. 2018.

Hunter, et al., "IL-6 as a Keystone Cytokine in Health and Disease", Nature Immunology, vol. 16, No. 5, pp. 448-457, May 2015.

Imagawa et al., "Safety and efficacy of tocilizumab, an anti-IL-6-receptor monoclonal antibody, in patients with polyarticular-course juvenile idiopathic arthritis", Modern Rheumatology, Jun. 12, 2011, 22(1): 109-115.

International Search Report and Written Opinion for PCT International Patent Application No. PCT/US2020/016203, mailed Jul. 14, 2020.

International Search report and Written Opinion for PCT International Patent Application No. PCT/US2020/035871, mailed on Sep. 28, 2020.

International Search Report and Written Opinion received for PCT Patent Application No. PCT/US2016/060344, mailed on Mar. 13, 2017.

International Search Report and Written Opinion Received for PCT Application No. PCT/US2020/037325, mailed on Oct. 27, 2020.

International Search Report and Written Opinion received for PCT Patent Application No. PCT/IB2021/054546, mailed on Sep. 14, 2021.

International Search Report and Written Opinion received for PCT Patent Application No. PCT/IB2021/054652, mailed on Aug. 30, 2021.

International Search Report and Written Opinion received for PCT Patent Application No. PCT/US2017/021149, mailed on Jul. 18, 2017.

International Search Report and Written Opinion received for PCT Patent Application No. PCT/US2020/029930, mailed on Oct. 8, 2020.

International Search Report with Written Opinion corresponding to International Patent Application No. PCT/US2023/065361, mailed Jul. 14, 2023.

Jones, et al., Comparison of Tocilizumab Monotherapy Versus Methotrexate Monotherapy in Patients With Moderate to Severe Rheumatoid Arthritis: the AMBITION Study, Annals of the Rheumatic Diseases, vol. 69, No. 01, pp. 88-96, 2010.

Kaneko, Tocilizumab in Rheumatoid Arthritis: Efficacy, Safety and Its Place in Therapy, Therapeutic Advances in Chronic Disease, vol. 4, No. 1, pp. 15-21, 2013.

Karmakar, et al., "Bone Damage in Rheumatoid Arthritis—Mechanistic Insights and Approaches to Prevention", Rheumatic Diseases Clinics of North America, vol. 36, No. 2, 19 Pages, May 1, 2010.

Kawashima, et al., "Soluble IL-6 Receptor In Vitreous Fluid Of Patients With Proliferative Diabetic Retinopathy", Japanese Journal of Ophthalmology, vol. 51, No. 2, pp. 100-104, Apr. 6, 2007.

Khan, et al., Determinants of Discordance in Patients' and Physicians' Rating of Rheumatoid Arthritis Disease Activity, Arthritis Care & Research (Hoboken), vol. 64, No. 2, pp. 206-214, 2012.

Kimel et al., "Adalimumab plus methotrexate improved SF-36 scores and reduced the effect of rheumatoid arthritis (RA) on work activity for patients with early RA", The Journal of Rheumatology, Feb. 2008, 35(2): 206-215.

Kishimoto, et al., "Interleukin-6 (IL-6)", The Cytokine Handbook. Ed.: Thomson. Academic Press. London, United Kingdom, vol. 12, pp. 281-304, Jan. 1, 2003.

(56) References Cited

OTHER PUBLICATIONS

Klein, et al. FRI0549—Efficacy and Safety of Tocilizumab in Systemic and Polyarticular Juvenile Idiopathic Arthritis—Data of Toe Biker Registry Squibb, Johnson & Johnson, Novartis, Pfizer, Fieckitt Benkiser, and Roche Jun. 14, 2019 pp. 969-970.
Kojima, et al., Depression, Inflammation, and Pain in Patients With Rheumatoid Arthritis, Arthritis & Rheumatism (Arthritis Care & Research), vol. 61, No. 8, pp. 1018-1024, Aug. 15, 2009.
Kremer, et al., Tocilizumab Inhibits Structural Joint Damage in Rheumatoid Arthritis Patients With Inadequate Responses to Methotrexate, Arthritis & Rheumatism vol. 63, No. 3, pp. 609-621, 2011.
Kringelbach, et al., "Identification of New Biomarkers to Promote Personalised Treatment of Patients with Inflammatory Rheumatic Disease: Protocol for an Open Cohort Study", British Medical Journal Open, vol. 8, e019325, pp. 1-8., Feb. 1, 2018.
Kristensen, et al., Is Swollen to Tender Joint Count Ratio a New and Useful Clinical Marker for Biologic Drug Response in Rheumatoid Arthritis? Results From a Swedish Cohort, Arthritis Care & Research (Hoboken), vol. 66, No. 2, pp. 173-179, 2014.
Lamb et al., "Sarilumab: A Review in Moderate to Severe Rheumatoid Arthritis Drugs", Drugs, 2018, 78: 929-940.
Lee et al., "Disease modifying drugs in adult rheumatoid arthritis", Australian Prescriber, Apr. 2003, 26: 36-40.
Lee, et al., Pain Persists in DAS28 Rheumatoid Arthritis Remission but Not in ACR/EULAR Remission: a Longitudinal Observational Study, Arthritis Research & Therapy, vol. 13, No. R83, pp. 1-9, 2011.
Lin, "Targeting Interleukin-6 For Noninfectious Uveitis, Clinical Ophthalmology", vol. 9, pp. 1697-1702, Sep. 1, 2015.
Lipsky, "Interleukin-6 and Rheumatic Diseases", Arthritis Research & Therapy, vol. 8, Suppl 2, S4, pp. 1-5, Jan. 1, 2006.
Lourdudoss et al., "Dietary intake of polyunsaturated fatty acids and pain in spite of inflammatory control among methotrexate-treated early rheumatoid arthritis patients", Arthritis Care and Research, Feb. 2018, 70(2): 205-212.
Maini, et al., Double-blind Randomized Controlled Clinical Trial of the Interleukin-6 Receptor Antagonist, Tocilizumab, in European Patients With Rheumatoid Arthritis Who Had an Incomplete Response to Methotrexate, Arthritis & Rheumatism, vol. 54, No. 9, pp. 2817-2829, Aug. 31, 2006.
Maini, et al., Infliximab (Chimeric Anti-Tumour Necrosis Factor A Monoclonal Antibody) Versus Placebo in Rheumatoid Arthritis Patients Receiving Concomitant Methotrexate: a Randomised Phase III Trial, The Lancet, vol. 354, No. 9194, pp. 1932-1939, 1999.
Matcham, et al., Psychological Correlates of Fatigue in Rheumatoid Arthritis: A Systematic Review, Clinical Psychology Review, vol. 39, pp. 16-29, Jul. 2015.
Matcham, et al., Symptoms of Depression and Anxiety Predict Treatment Response and Long-term Physical Health Outcomes in Rheumatoid Arthritis: Secondary Analysis of a Randomized Controlled Trial, Rheumatology, vol. 55, Issue 2, pp. 268-278, Feb. 2016.
Matcham, et al., The Prevalence of Depression in Rheumatoid Arthritis: A Systematic Review and Meta-analysis, Rheumatology, vol. 52, Issue 12, pp. 2136-2148, Sep. 3, 2013.
Matteson, "Current Treatment Strategies for Rheumatoid Arthritis", Mayo Clinic Proceedings, vol. 75, pp. 69-74, Jan. 2000.
Mcgovern, (Oct. 19, 2016) "Center for Drug Evaluation and Research", Application No. 761037Orig1s000, pp. 01-278.
Mcinnes, et al., "Cytokines in the Pathogenesis of Rheumatoid Arthritis", Nature Reviews, Immunology, vol. 7, pp. 429-442, Jun. 2007.
Mcwilliams, et al., Pain Mechanisms in Rheumatoid Arthritis, Clinical and Experimental Rheumatology, vol. 35, No. 5, pp. S94-S101, 2017.
Medscape, Actemra, Retrieved online: <URL: https://reference.medscape.com/drug/actennra-tocilizunnab-999419>, Retrieved on Feb. 8, 2022.
Merida, et al., "New Immunosuppressive Therapies in Uveitis Treatment", International Journal of Molecular Sciences, vol. 16, No. 8, pp. 18778-18795, Aug. 11, 2015.
Mesquida, et al., "Long-Term Effects of Tocilizumab Therapy for Refractory Uveitis-Related Macular Edema", Ophthalmology, vol. 121, No. 12, pp. 2380-2386, Sep. 6, 2014.
Millar et al., Inflammatory mechanisms in tendinopathy—towards translation, Nature, Feb. 2017, 13: 110-122.
Montaño et al., "Influence of the Isotype of the Light Chain on the Properties of IgG", Journal of Immunology, 2002, 168: 224-231.
Muszbek et al., "Economic Evaluation of Sarilumab in the Treatment of Adult Patients with Moderately-to-Severely Active Rheumatoid Arthritis Who Have an Inadequate Response to Conventional Synthetic Disease-Modifying Antirheumatic Drugs", Advances in Therapy, Apr. 19, 2019, 36(6): 1337-1357.
Nadkarni, et al., Incidence of Dose Escalation and Impact on Biologic Costs Among Patients With Rheumatoid Arthritis Treated With Three Intravenous Agents, Journal of Comparative Effectiveness Research, vol. 6, No. 8, pp. 671-682, 2017.
Nasonov, E.L. et al., "Prospects of pharmacotherapy rheumatoid arthritis: monoclonal antibodies", Nauchnopraktych Rheumatol., 2012, 52(3): 75-82.
NCBI, C-Reactive Protein Isoform 1 Precursor [*Homo sapiens*], NCBI Reference Sequence: NP_001315986.1, Retrieved from: <<https://www.ncbi.nlm.nih.gov/protein/NP_001315986.1>>, pp. 1-3, Jun. 29, 2016.
NCBI, C-X-C Motif Chemokine 13 Precursor [*Homo sapiens*], NCBI Reference Sequence: NP_006410.1, Retrieved from: <<https://www.ncbi.nlm.nih.gov/protein/NP_006410.1>>, pp. 1-3.
NCBI, Intercellular Adhesion Molecule 1 Precursor [*Homo sapiens*], NCBI Reference Sequence: NP_000192.2, Retrieved from: <<https://www.ncbi.nlm.nih.gov/protein/NP_000192.2>>, pp. 1-4, Feb. 8, 2008.
NCBI, Matrix Metallopeptidase 3 (Stromelysin 1, Progelatinase) [*Homo sapiens*], NCBI Reference Sequence: EAW67032.1, Retrieved from: <<https://www.ncbi.nlm.nih.gov/protein/EAW67032.1>>, pp. 1-2, Mar. 23, 2015.
NCBI, PubChem SID: 135626879, National Library of Medicine, Apr. 5, 2012, Retrieved from: <<https://pubchem.ncbi.nlm.nih.gov/substance/135626879>>.
NCBI, Serum Amyloid A [*Homo sapiens*], NCBI Reference Sequence: AAB24060.1, Retrieved from: <<https://www.ncbi.nlm.nih.gov/protein/AAB24060.1>>, 1 Page, Jul. 28, 2016.
New Drug Approvals Retrieved from: <<https://www.drugs.com/newdrugs.html>> pp. 1-7, 2019.
Nguyen et al., "The SATURN Study (SARIL-NIU): Sarilumab for the Treatment of Posterior Segment Non-Infectious Uveitis (NIU)", Investigative Ophthalmology & Visual Science, vol. 56, No. 7, 3116, Jun. 2015.
Nicassio, et al. (Jan. 2012) "The Contribution of Pain and Depression to Self-Reported Sleep Disturbance in Patients with Rheumatoid Arthritis", Pain, vol. 153, No. 1, pp. 107-112.
Nieminen, et al., "The Use of the ATF System to Culture Chinese Hamster Ovary Cells in a Concentrated Fed-Batch System", BioPharm International, vol. 24, Issue 6, pp. 1-8, Jun. 1, 2011.
Nishimoto, et al., Humanized Antihuman IL-6 Receptor Antibody, Tocilizumab, Part of the Handbook of Experimental Pharmacology, vol. 181, Therapeutic Antibodies, pp. 151-160, 2008.
Non-Final Office Action received for U.S. Appl. No. 13/648,521, mailed on Jul. 3, 2014.
Non-Final Office Action received for U.S. Appl. No. 13/648,521, mailed on Jun. 26, 2015.
Non-Final Office Action received for U.S. Appl. No. 13/648,521, mailed on Mar. 19, 2015.
Non-Final Office Action received for U.S. Appl. No. 13/648,521, mailed on Oct. 18, 2013.
Non-Final Office Action received for U.S. Appl. No. 14/350,973, mailed on Feb. 5, 2016.
Non-Final Office Action received for U.S. Appl. No. 14/350,973, mailed on Oct. 18, 2019.
Notice of Allowance received for U.S. Appl. No. 14/350,973, mailed on Jun. 14, 2016.

(56) References Cited

OTHER PUBLICATIONS

Nussenblatt, et al., "Standardization of Vitreal Inflammatory Activity in Intermediate And Posterior Uveitis", Ophthalmology, vol. 92, No. 4, pp. 467-471, Apr. 1, 1985.
Ogata et al., "Phase III Study of the Efficacy and Safety of Subcutaneous Versus Intravenous Tocilizumab Monotherapy in Patients With Rheumatoid Arthritis", Arthritis Care & Research, Aug. 27, 2013, vol. 66, No. 3, pp. 344-354.
Ogata, et al., Long-term Safety and Efficacy of Weekly Subcutaneous Tocilizumab Monotherapy in Patients With Rheumatoid Arthritis Who Had an Inadequate Response to Subcutaneous Tocilizumab Every Other Week: Results From the Open-label Extension of the SHINOBI Study, Modern Rheumatology, vol. 29, Issue 5, pp. 767-774, Sep. 3, 2019.
Ogata, et al., Subcutaneous Tocilizumab: Recent Advances for the Treatment of Rheumatoid Arthritis, Expert Opinion on Drug Delivery, vol. 16, Issue 6, pp. 639-648, Jun. 3, 2019.
Ohta, et al., Optimal Dose Prediction by Pharmacokinetic and Biomarker Response of Subcutaneous Tocilizumab Treatment A Phase I/II Study Evaluating the Safety, Pharmacokinetics and Clinical Response in Patients with Rheumatoid Arthritis, Arthritis & Rheumatism, vol. 62, Supplement 10, pp. 1-2, Oct. 1, 2010.
Ongkosuwito, et al., "Analysis of Immunoregulatory Cytokines in Ocular Fluid Samples From Patients With Uveitis", Investigative Ophthalmology & Visual Science, vol. 39, No. 13, pp. 2659-2665, Dec. 1, 1998.
Overman, et al., The Prospective Association Between Psychological Distress and Disease Activity in Rheumatoid Arthritis: a Multilevel Regression Analysis, Annals of the Rheumatic Diseases, vol. 71, No. 2, pp. 192-197, 2012.
Pappas, et al., Dosing of Intravenous Tocilizumab in a Real-World Setting of Rheumatoid Arthritis: Analyses from the Corrona Registry, Rheumatology and Therapy, vol. 3, pp. 103-115, Feb. 8, 2016.
Patel et al., "The Negative Effect of Carpal Tunnel Syndrome on Sleep Quality", Sleep Disorders, Feb. 17, 2014, Article ID 962746.
Paul et al., "Effectiveness of biologic and non-biologic antirheumatic drugs on anaemia markers in 153,788 patients with rheumatoid arthritis: New evidence from real-world data", Seminars in Arthritis and Rheumatism, Feb. 1, 2018, vol. 47, No. 4, pp. 478-484.
Peichl, "Biologikatherapie in der Rheumatologie", DoctorConsult—The Journal. Wissen fur Klinik und Praxis, Nov. 2011, 2(3): e164-e166.
Pelechas et al., "Clinical evaluation of the safety, efficacy and tolerability of sarilumab in the treatment of moderate to severe rheumatoid arthritis", Therapeutics and Clinical Risk Management, Sept. 1, 2019, vol. 15, pp. 1073-1079.
Perez, et al., "Elevated Levels Of Interleukin 6 In The Vitreous Fluid Of Patients With Pars Planitis And Posterior Uveitis: The Massachusetts Eye & Ear Experience And Review Of Previous Studies", Ocular Immunology and Inflammation, vol. 12, No. 3, pp. 193-201, Sep. 2004.
Pham et al., "Patient acceptable symptomatic state (PASS)", Joint Bone Spine, Jul. 2009, 76(4): 321-323.
Pincus, Limitations of a Quantitative Swollen and Tender Joint Count to Assess and Monitor Patients with Rheumatoid Arthritis, Bulletin of the NYU Hospital for Joint Diseases, 2008, 66(3): 216-223.
Pollard, et al., Fibromyalgic Rheumatoid Arthritis and Disease Assessment, Rheumatology, vol. 49, No. 5, pp. 924-928, Jan. 25, 2010.
Pulawski et al., "Certain therapies linked to pulmonary toxicity among patients with rheumatic diseases", Healio, May 20, 2015, obtained from url: https://www.healio.com/news/rheumatology/20150520/certain-therapies-linked-to-pulmonary-toxicity-among-patients-with-rheumatic-diseases.
Rafique, et al., "Evaluation of The Binding Kinetics and Functional Bioassay Activity Of Sarilumab And Tocilizumab To The Human IL-6 Receptor (IL-6r) alpha", Annals of the Rheumatic Diseases, vol. 72, Issue Suppl 3, pp. A797.1-A797, Jun. 23, 2013.
Raimondo et al., "Profile of sarilumab and its potential in the treatment of rheumatoid arthritis", Drug Design, Development and Therapy, May 24, 2017, 11: 1593-1603.
Restriction Requirement received for U.S. Appl. No. 13/648,521, mailed on Jun. 10, 2013, 7 Pages.
Restriction Requirement received for U.S. Appl. No. 14/350,973, mailed on Aug. 19, 2015, 8 Pages.
Riancho-Zarrabeitia, et al., "Efficacy of Tocilizumab in Patients with Uveitis Refractory to Other Biologic Drugs: A Multicenter Study on 31 Cases", 2014 ACR/ARHP Annual Meeting Abstract No. 1249, Retrieved from: <<https://acrabstracts.org/abstract/efficacy-of-Tocilizumab-in-patients-with-uveitis-refractory-to-other-biologic-drugs-a-multicenter-study-on-31-cases/>>, Retrieved on Sep. 14, 2020.
Roche, Anti-Human IL-6 Receptor Monoclonal Antibody "Actemra" Subcutaneous Injection Demonstrates Efficacy in Rheumatoid Arthritis in Phase III Clinical Study, Jul. 19, 2011, Retrieved online: <URL: https://www.roche.com/dann/jcr:c49f4e4e-d60e-48cc-a14e-c0f1f4107b24/en/inv-update-2011-07-19b-annex.pdf>, Retrieved on Feb. 8, 2022.
Rose-John, et al., "Interleukin-6 Biology is Coordinated by Membrane-Bound and Soluble Receptors: Role in Inflammation and Cancer", Journal of Leukocyte Biology, vol. 80, No. 2, pp. 227-236, May 17, 2006.
Salaffi et al. "The health-related quality of life in rheumatoid arthritis, ankylosing spondylitis, and psoriatic arthritis: a comparison with a selected sample of healthy people", Health and Quality of Life Outcomes, Biomed Central, vol. 7, No. 1, pp. 25, 2009.
Sarzi-Puttini, et al., Correlation of the Score for Subjective Pain With Physical Disability, Clinical and Radiographic Scores in Recent Onset Rheumatoid Arthritis, BMC Musculoskeletal Disorders, vol. 3, No. 18, pp. 1-4, Jul. 19, 2002.
Schaible, Nociceptive Neurons Detect Cytokines in Arthritis, Arthritis Research & Therapy, vol. 16, No. 470, pp. 1-9, 2014.
Schett, "Physiological Effects of Modulating the Interleukin-6 Axis", Rheumatology, vol. 57, Supplement 2, pp. ii43-ii50, Feb. 1, 2018.
Schett, et al., "Bone Erosion in Rheumatoid Arthritis: Mechanisms, Diagnosis and Treatment", Nature Reviews Rheumatology, vol. 8, No. 11, 22 Pages, Nov. 2012.
Scott, "Sarilumab: First Global Approval", Drugs, 2017, 77: 705-712.
Sebba et al., "Comparative Effectiveness of TNF Inhibitor vs IL-6 Receptor Inhibitor as Monotherapy or Combination Therapy with Methotrexate in Patients with Rheumatoid Arthritis: Analysis from the CorEvitas RA Registry", Poster No. 0834, ACR Convergence—Virtual, Nov. 1-10, 2021.
Sebba, "Comparative Effectiveness of TNF Inhibitor vs IL-6 Receptor Inhibitor as Monotherapy or Combination Therapy with Methotrexate in Patients with Rheumatoid Arthritis: Analysis from the CorEvitas RA Registry", SAR-54318 TNFi/IL-6Ri Mono/Combo Audio narration, ACR Convergence—Virtual, Nov. 1-10, 2021.
Sechidis, et al., "Distinguishing Prognostic and Predictive Biomarkers: An Information Theoretic Approach", Bioinformatics, vol. 34, No. 19, pp. 3365-3376, Oct. 1, 2018.
Seth, et al., "Development of a New Bioprocess Scheme Using Frozen Seed Train Intermediates to Initiate CHO Cell Culture Manufacturing Campaigns", Biotechnology and Bioengineering, May 2013, vol. 110, Issue 5, pp. 1376-1385.
Singh, et al., 2015 American College of Rheumatology Guideline for the Treatment of Rheumatoid Arthritis, Arthritis & rheumatology, vol. 68, No. 1, pp. 1-26, 2016.
Smolen et al., "Rheumatoid arthritis", Lancet, 2016, 388(10055): 2023-2038.
Smolen, et al., "The Assessment of Disease Activity in Rheumatoid Arthritis", Clinical and Experimental Rheumatology, vol. 28, Supplement 59, pp. S18-S27, May 1, 2010.
Smolen, et al., EULAR Recommendations for the Management of Rheumatoid Arthritis With Synthetic and Biological Disease-modifying Antirheumatic Drugs: 2016 Update, Annals of the Rheumatic Diseases, vol. 76, No. 6, pp. 960-977, 2017.
Solomon, et al., "Patterns of Cardiovascular Risk in Rheumatoid Arthritis", Annals of the Rheumatic Diseases, vol. 65, pp. 1608-1612, Dec. 1, 2006.

(56) References Cited

OTHER PUBLICATIONS

Song, et al., "Comparative Evaluation of the Effects of Treatment With Tocilizumab and TNF-α Inhibitors on Serum Hepcidin, Anemia Response and Disease Activity in Rheumatoid Arthritis Patients", Arthritis Research & Therapy, vol. 15, Article No. R141, pp. 1-10, Oct. 1, 2013.
Spectrum Laboratories, Inc., "Hollow Fiber Filters", Datasheet [online], Spectrumlabs.com, Copyright 1995-2015, Retrieved from: <<URL: http://www.spectrumlabs.com/filtration/mPESKrosFloList.html>>, Retrieved on: Jun. 12, 2015.
Stamp et al., "The use of low dose methotrexate in rheumatoid arthritis—are we entering a new era of therapeutic drug monitoring and pharmacogenomics?", Biomedicine & Pharmacotherapy, 2006, 60: 678-687.
Steel et al., "2015 EULAR-ACR recommendations for polymyalgia rheumatica: the message and next steps", Rheumatology, Jun. 17, 2016, 55(6): 955-956, Advance Access Publication Dec. 17, 2015.
Strand et al., "Patient-reported outcomes from a randomized phase III trial of sarilumab monotherapy versus adalimumab monotherapy in patients with rheumatoid arthritis", Arthritis Res Ther., 2018, 20(1): 129.
Strand, et al., "Health-related Quality of Life Outcomes of Adalimumab for Patients with Early Rheumatoid Arthritis: Results from a Randomized Multicenter Study", The Journal of Rheumatology, vol. 39, pp. 63-72, Jan. 1, 2012.
Strand, et al., Sarilumab Improves Patient-reported Outcomes in Rheumatoid Arthritis Patients With Inadequate Response/Intolerance to Tumour Necrosis Factor Inhibitors, RMD Open, vol. 3, e000416, 2017.
Strand, et al., Sarilumab Plus Methotrexate Improves Patient-reported Outcomes in Patients With Active Rheumatoid Arthritis and Inadequate Responses to Methotrexate: Results of a Phase III Trial, Arthritis Research & Therapy, vol. 18, No. 198, pp. 1-10, 2016.
Studenic, et al., Discrepancies Between Patients and Physicians in Their Perceptions of Rheumatoid Arthritis Disease Activity, Arthritis & Rheumatology, vol. 64, No. 9, pp. 2814-2823, 2012.
Study of the Safety, Tolerability, and Bioactivity of Tocilizumab On Patients With Non-infectious UVEITIS, The STOP-UVEITIS Study, ClinicalTrials.gov Archive, Oct. 29, 2012.
Suttorp-Schulten, et al., "Recent Developments In The Treatment Of Posterior Uveitis", Ocular Immunology and Inflammation, vol. 4, No. 4, pp. 207-217, 1996.
Świerkot et al., "Methotrexate in rheumatoid arthritis", Pharmacological Reports, 2006, 58: 473-492.
Taylor, et al., "A Transgenic Mouse That Expresses a Diversity of Human Sequence Heavy and Light Chain Immunoglobulins", Nucleic Acids Research, vol. 20, No. 23, pp. 6287-6295, Dec. 11, 1992.
Taylor, et al., Patient Perceptions Concerning Pain Management in the Treatment of Rheumatoid Arthritis, The Journal of International Medical Research, vol. 38, No. 4, pp. 1213-1224, 2010.
Turnier et al., "Tocilizumab for treating juvenile idiopathic arthritis", Expert Opinion on Biological Therapy, 2016, 16(4): 559-566.
Ueno et al., "3-145: The efficacy and safety of additional tocilizumab in patients with polymyalgia rheumatica resistant to or intolerant of conventional therapy", AU, Apr. 1, 2019, 22(S3): 204.
United States Census Bureau. Census Regions and Divisions of the United States, Retrieved from: <<https://www2.census.gov/geo/pdfs/maps-data/maps/reference/us_regdiv.pdf>>, Accessed on: Apr. 8, 2019.
Valentincic, et al., "Intraocular And Serum Cytokine Profiles In Patients With Intermediate Uveitis", Molecular Vision, vol. 17, pp. 2003-2010, Jul. 20, 2011.
Van Herwaarden, et al., Dose Reduction of Tocilizumab in Rheumatoid Arthritis Patients With Low Disease Activity, Clinical and Experimental Rheumatology, vol. 32, pp. 390-394, 2014.
Van Vollenhoven, Sex Differences in Rheumatoid Arthritis: More Than Meets the Eye, BMC Medicine, vol. 7, No. 12, pp. 1-4, Mar. 30, 2009.
Walsh, et al., Mechanisms, Impact and Management of Pain in Rheumatoid Arthritis, Nature Reviews Rheumatology, vol. 10, No. 10, pp. 581-592, 2014.
Wei et al., "Serum Levels of IL-6 and TNF-α May Correlate with Activity and Severity of Rheumatoid Arthritis", Med Sci Monit., 2015, 21: 4030-4038.
Wells, et al., "Immunogenicity of Sarilumab Monotherapy in Patients with Rheumatoid Arthritis Who Were Inadequate Responders or Intolerant to Disease-Modifying Antirheumatic Drugs", Rheumatology and Therapy, vol. 6, No. 3, pp. 339-352, May 14, 2019.
Wiens, et al., "A Systematic Review and Meta-Analysis of the Efficacy and Safety of Adalimumab for Treating Rheumatoid Arthritis", Rheumatology International, vol. 30, Issue 8, pp. 1063-1070, Jun. 1, 2010.
Wolfe et al., "Sleep Disturbance in Patients with Rheumatoid Arthritis: Evaluation by Medical Outcomes Study and Visual Analog Sleep Scales", J Rheumatol., 2006, 33:1942-1951.
Woods, et al., "Container System for Enabling Commercial Production of Cryopreserved Cell Therapy Products", Regenerative Medicine, vol. 5, No. 4, pp. 659-667, Jul. 15, 2010.
Yamamura, "FRI0266. The Real-World Efficacy of the 2015 EULAR/ACR Recommendations for the Management of Polymyalgia Rheumatica with Additional Tocilizumab Therapy", Annals of the Rheumatic Diseases, Jun. 13, 2020, 79(Suppl 1), 717.2-718.
Yang, et al., Chronic Pain: Structural and Functional Changes in Brain Structures and Associated Negative Affective States, International Journal of Molecular Sciences, vol. 20, No. 13, p. 3130, Jun. 26, 2019.
Yokota et al., "Efficacy and safety of tocilizumab in patients with systemic-onset juvenile idiopathic arthritis: a randomised, double-blind, placebo-controlled, withdrawal phase III trial", The Lancet, Mar. 22, 2008, 371(9617): pp. 998-1006.
Yoo et al., "Exosomal amyloid A and lymphatic vessel endothelial hyaluronic acid receptor-1 proteins are associated with disease activity in rheumatoid arthritis", Arthritis Research & Therapy, 2017, 19(1): 119.
Yoshii, I. et al., "Influence of pain score measured by a visual analog scale (PS-VAS) on the Health Assessment Questionnaire Disability Index and 28 joint-Disease Activity Index with C-reactive protein in rheumatoid arthritis patients", Int J, Rheum DID, 2018, 21: 1955-1961.
Yoshimura, et al., "Comprehensive Analysis of Inflammatory Immune Mediators in Vitreoretinal Diseases", PLoS One, vol. 4, No. 12, pp. 1-9, Jan. 1, 2009.
Zhou, et al., Interleukin-6: An Emerging Regulator of Pathological Pain, Journal of Neuroinflammation, vol. 13, No. 141, pp. 1-9, 2016.S.
Choy et al., "Subcutaneous tocilizumab in rheumatoid arthritis: findings from the common-frame work phase 4 study programme TOZURA conducted in 22 countries", Rheumatology, Mar. 1, 2018, 57(3): 499-507.
ClinicalTrials.gov, "Efficacy, Safety and Tolerability of Repeated Dosis of Intravitreous Bevacizumab in Uveitic Macular Oedema", ClinicalTrials.gov ID: NCT01095809, Mar. 23, 2012.
ClinicalTrials.gov. (Jan. 17, 2017) "A Study of the Efficacy and Safety of Tocilizumab in Adults With Rheumatoid Arthritis", ClinicalTrials.gov. Identifier: NCT01988012.
ClinicalTrials.gov. (May 11, 2016) "A Study to Compare Subcutaneous Versus Intravenous Administration of RoActemra/Actemra (Tocilizumab) in Participants With Moderate to Severe Active Rheumatoid Arthritis", ClinicalTrials.gov. Identifier: NCT01194414.
ClinicalTrials.gov. (Sep. 15, 2014) "TORPEDO Study: A Study on Rapid Effect of Tocilizumab in Patients With Rheumatoid Arthritis With an Inadequate Response to Disease-Modifying Antirheumatic Drugs (DMARDs) or Anti-TNF", ClinicalTrials.gov. Identifier: NCT00977106.
Emery et al., "Evidence-based review of biologic markers as indicators of disease progression and remission in rheumatoid arthritis", Rheumatol Int., Jul. 2007, 27(9): 793-806, Epublished May 16, 2007.

(56) References Cited

OTHER PUBLICATIONS

Heissigerova et al., "Efficacy and Safety of Sarilumab for the Treatment of Posterior Segment Noninfectious Uveitis (SARIL-NIU):: The Phase 2 SATURN Study", Opthamology, Mar. 2019, 126(3): 428-437.
Huizen et al., "What does it mean if you have a high C-reactive protein level?", Medical News Today, Oct. 11, 2023.
Izumi et al., "Steroid-Sparing Effect of Tocilizumab and Methotrexate in Patients with Polymyalgia Rheumatica: A Retrospective Cohort Study", Journ Clin Med., Jun. 30, 2021, 10: 2948.
Ohta et al., "Mechanism-Based Approach Using a Biomarker Response to Evaluate Tocilizumab Subcutaneous Injection in Patients With Rheumatoid Arthritis With an Inadequate Response to Synthetic DMARDs (MATUSRI Study)", The Journal of Clinical Pharmacology, Jan. 2014, 54(1):109-119, Epublished Oct. 12, 2013.
Starkova et al., "ES02. Relatonship between fatigue and IL 6, diseas activity, depression in patients treated with tocilizumab", Rheumatology, Feb. 2012, 51(Suppl 1): i34-i41, Published Jan. 10, 2012.
Starkova et al., "Impact of tocilizumab therapy on fatigue in patients with rheumatoid arthritis", Scientific and Practical Rheumatology, 2012, N 52(3): 33-37, English translation included.
Takeuchi, "Rheumatoid Arthritis: Advances in Diagnosis and Treatment", The Journal of the Japanese Society of Internal Medicine, 2012, vol. 101, pp. 2815-2817.
Teper et al., "Update on the Management of Uveitic Macular Edema", J Clin Med., 2021, 10(18): 4133.
Unknown, "Differentiation of Arthritis: Advances in Diagnosis and Treatment 1. Rheumatoid Arthritis", The Journal of the Japanese Society of Internal Medicine, 2010, vol. 99, pp. 2392-2400.
Avdeeva et al., "Idiopathic Fibrosing Alveolitis", RMJ, Respiratory Diseases, Feb. 17, 1998, 4: 4.
Bharucha et al., "Growth During Tocilizumab Therapy for Polyarticular-course Juvenile Idiopathic Arthritis: 2-year Data from aPhase III Clinical Trial", The Journal of Rheumatology, Jul. 1, 2018, 745(8): 1173-1179.
Boleto et al., "Safety of combination therapy with two bDMARDs in patients with rheumatoid arthritis: A systematic review and meta-analysis", Seminars in Arthritis and Rheumatism, Aug. 2019, 49(1): 35-42.
Chambers et al., "Serum Amyloid A Protein Concentration In Rheumatoid Arthritis And Its Role In Monitoring Disease Activity", Annals Of The Rheumatic Diseases, Jan. 1, 1983, 42(6): 665-667.
Choi, "Issue & Trend: Rheumatoid Arhtritis", Korea Pharmaceutical Information Center, 2000. In Korean.
ClinicalTrials.gov (Jun. 18, 2021) "A Randomized, Double-blind, Placebo-controlled Study to Evaluate the Efficacy and Safety of Sarilumab in Patients With Polymyalgia Rheumatica", ClinicalTrials.gov ID NCT03600818.
ClinicalTrials.gov (May 21, 2020) "Efficacy and Safety of GSK3196165 (Otilimab) Versus Placebo and Sarilumab in Participants With Moderately to Severely Active Rheumatoid Arthritis Who Have an Inadequate Response to Biological Disease-modifying Antirheumatic Drug (DMARDs) and/or Janus Kinase (JAK) Inhibitors (contRAst 3)", ClinicalTrials.gov Identifier: NCT04134728.
ClinicalTrials.gov. (Sep. 27, 2011) "Effect of SAR153191 (REGN88) With Methotrexate in Patients With Active Rheumatoid Arthritis Who Failed INF-a Blockers," Study Details, ClinicalTrials.gov Identifier: NCT01217814.
Corraliza-Gorjón et al., "New strategies using antibody combinations to increase cancer treatment effectiveness", Frontiers in immunology, 2017, 8: 1804.
Holm et al., "In diabetic retinopathy, foveal thickness of 300 mum seems to correlate with functionally significant loss of vision", Doc Ophthalmol., May 2007, 114(3): 117-124.
Kenny et al., "Therapeutic protein drug-drug interactions: navigating the knowledge gaps—highlights from the 2012 AAPS NBC Roundtable and IQ Consortium/FDA workshop", The AAPS Journal, 2013, 15(4): 933-940.
Lee, "A review of sarilumab for the treatment of rheumatoid arthritis", Immunotherapy, Oct. 18, 2017, 10(1): 57-65.
Mccreary et al., "Development and Validation of a Targeted Next-Generation Sequencing Gene Panel for Children With Neuroinflammation", JAMA Network Open, Oct. 30, 2019, 2(10): e1914274.
Mould et al., "Pharmacokinetics and pharmacodynamics of monoclonal antibodies", BioDrugs, 2010, 24(1): 23-39.
Ohtsubo et al., "Effective combination therapy of TNF antagonists with DMARDs", Nihon Rinsho, Jul. 2007, 65(7): 1287-1291. In Japanese with English abstract.
Prodanovic et al., "Matrix Metalloproteinases-3 Baseline Serum Levels in Early Rheumatoid Arthritis Patients without Initial Radiographic Changes: A TwoYear Ultrasonographic Study", Med Princ Pract., 2018, 27(4): 378-386, Epublished May 24, 2018.
Sack Jr et al., "Serum amyloid A—a review", Mol Med., Aug. 30, 2018, 24(1): 46.
Sanofi KK, Kezvara for Subcutaneous Injection Report on the Deliberation Results, Pharmaceutical Evaluation Division, Pharmaceutical Safety and Environmental Health Bureau Ministry of Health, Labour, and Welfare, Non-proprietary Name: Sarilumab (genetical Recombination) (JAN*), Date of Application: Oct. 7, 2016.
Santos et al., "Degree of decrease in central retinal thickness predicts visual acuity response to intravitreal ranibizumab in diabetic macular edema", Ophthalmologica, 2014, 231(1): 16-22.
Tallarida et al., "Quantitative Methods for Assessing Drug Synergism", Genes & Cancer, 2011, 2(11): 1003-1008.
Targonska-Stepniak et al., "Serum Amyloid A as a Marker of Persistent Inflammation and an Indicator of Cardiovascular and Renal Involvement in Patients with Rheumatoid Arthritis", Mediators of Inflammation, Jan. 1, 2014.
Tyagi et al., "Chemical Modification and Chemical Crosslinking for Protein/Enzyme Stabilization", Biokhimiya, 1998, 63(3): 395-407.
Yukawa et al., "ACR2008 Recommendation: Treatment Strategy for rheumatoid arthritis based on ACR2008 recommendations", Journal of Clinical and Experimental Medicine, 2010, 234(1): 30-36. In Japanese.
"Highlights of Prescribing Information" for ACTEMRA (tocilizumab), Reference ID: 5639738, Retrieved from url: <https://www.accessdata.fda.gov/drugsatfda_docs/label/2025/125276s149lbl.pdf>, Revised Aug. 2025.
"Highlights of Prescribing Information" for KEVZARA (sarilumab), US Approval: 2017, Revised May 2025, Retrieved from url: <https://products.sanofi.us/kevzara/kevzara.pdf>.
Ciubotariu et al., "Joint Damage Progression in Patients with Rheumatoid Arthritis in Clinical Remission. Do Biologics Perform Better Than Synthetic Antirheumatic Drugs?", Journal of Rheumatology, 2014, 41(8): 1576-1582.
ClinicalTrials.gov (Apr. 14, 2020) "A Randomized, Double-blind, Placebo-controlled Study to Evaluate the Efficacy and Safety of Sarilumab in Patients With Polymyalgia Rheumatica", ClinicalTrials.gov ID NCT03600818.
Den Broeder et al., "Non-Medical Switching from Tocilizumab to Sarilumab in Rheumatoid Arthritis Patients with Low Disease Activity: An Observational Study", Clin Pharmacol Ther., Oct. 2023, 114(4): 810-814, Epublished Jul. 27, 2023.
Gabay et al., "Sarilumab and adalimumab differential effects on bone remodelling and cardiovascular risk biomarkers, and predictions of treatment outcomes", Arthritis Research & Therapy, Apr. 7, 2020, 22: 70.
Papo et al., "Tocilizumab in severe and refractory non-infectious uveitis", Clinical and Experimental Rheumatology, 2014, 32(Suppl. 84): S75-79.
Rezaei et al., "In early rheumatoid arthritis, patients with a good initial response to methotrexate have excellent 2-year clinical outcomes, but radiological progression is not fully prevented: data from the methotrexate responders population in the SWEFOT trial", Ann Rheum Dis., 2012, 71: 186-191, Epublished Sep. 19, 2011.
Swets et al., "A comparison of the effectiveness of different doses of tocilizumab and sarilumab in the treatment of severe COVID-19: a natural experiment due to drug shortages", International Journal of Infectious Diseases, Apr. 2023, 129: 57-62.

(56) References Cited

OTHER PUBLICATIONS

U.S. Department of Health and Human Services—Food and Drug Administration, "Guidance for Industry—Rheumatoid Arthritis: Developing Drug Products for Treatment", May 2013, Clinical/Medical, Revision 1.

* cited by examiner

Part A

*Significant versus placebo by Cochran–Mantel–Haenszel test ($p<0.05$), correcting for multiplicity by Hommel's procedure

COMPOSITIONS FOR THE TREATMENT OF RHEUMATOID ARTHRITIS AND METHODS OF USING SAME

RELATED APPLICATIONS

This application is a continuation of U.S. patent application Ser. No. 14/350,973, filed Apr. 10, 2014, now U.S. Pat. No. 10,927,435, which is a 35 U.S.C. § 371 filing of International Patent Application No. PCT/EP2012/070052, filed Oct. 10, 2012, which claims priority to European Patent Application No. 12305889.3, filed Jul. 20, 2012, and U.S. Provisional Patent Application Ser. No. 61/545,864, filed Oct. 11, 2011, the entire disclosures of which are hereby incorporated herein by reference.

RELATED APPLICATIONS

This application is a continuation of U.S. patent application Ser. No. 14/350,973, filed Apr. 10, 2014, now U.S. Pat. No. 10,927,435, which is a 35 U.S.C. § 371 filing of International Patent Application No. PCT/EP2012/070052, filed Oct. 10, 2012, which claims priority to European Patent Application No. 12305889.3, filed Jul. 20, 2012, and U.S. Provisional Patent Application Ser. No. 61/545,864, filed Oct. 11, 2011, the entire disclosures of which are hereby incorporated herein by reference.

BACKGROUND

It is estimated that approximately 0.5% to 1% of the adult population in North America and Europe is affected by rheumatoid arthritis (RA). RA affects women twice as often as men and the incidence is highest among women over 40 years of age.

RA is characterized by persistent synovitis and progressive destruction of cartilage and bone in multiple joints. The hallmark of the disease is a symmetric polyarthritis characteristically involving the small joints of the hands and feet. The inflammatory process can also target other organs, characteristically bone marrow (anemia), eye (scleritis, episcleritis), lung (interstitial pneumonitis, pleuritis), cardiac (pericarditis) and skin (nodules, leukocytoclastic vasculitis). Systemic inflammation is characterized by laboratory abnormalities, such as anemia, elevated erythrocyte sedimentation rate, fibrinogen and C-reactive protein (CRP) and by clinical symptoms of fatigue, weight loss, muscle atrophy in affected joint areas. The presence of polyclonal high-titer rheumatoid factors and anticyclic citrullinated peptide (anti-CCP) antibodies provides evidence of immune dysregulation. It has been estimated that 65% to 70% of RA patients have progressive disease that leads to joint destruction, disability and premature death.

There is a need in the art for improved treatment regimens for the improvement of symptoms associated with RA.

SUMMARY

The present disclosure provides a method of treating rheumatoid arthritis in a subject in need thereof. The method includes administering to the subject an effective amount of sarilumab (SAR153191) and a member of the group consisting of leflunomide, sulfasalazine and hydroxychloroquine. In certain embodiments, the subject was previously ineffectively treated for rheumatoid arthritis by administering a TNF-α antagonist. Specifically, subject could have been treated for at least three months with the TNF-α antagonist or could have been intolerant of the TNF-α antagonist. The TNF-α antagonist could be etanercept, infliximab, adalimumab, golimumab or certolizumab. In other embodiments, the subject was previously ineffectively treated for rheumatoid arthritis by administering methotrexate.

The sarilumab could be administered at between 50 and 150 mg per week or between 100 and 200 mg per two weeks.

In certain specific embodiments, sarilumab and leflunomide are administered to the subject. The leflunomide can be administered orally. The leflunomide can also be administered at between 10 and 20 mg per day to the subject.

In other specific embodiments, sarilumab and sulfasalazine are administered to the subject. The sulfasalazine can be administered orally. The sulfasalazine can also be administered at between 1000 to 3000 mg per day to the subject.

In other specific embodiments, sarilumab and hydroxychloroquine are administered to the subject. The hydroxychloroquine can be administered orally. The hydroxychloroquine can also be administered at between 200 to 400 mg per day to the subject.

In some embodiments, as a result of the treatment, the subject achieves a 20% or 50% improvement in the American College of Rheumatology core set disease index after 12 weeks of treatment. In other embodiments, as a result of the treatment, the subject achieves a 20%, 50% or 70% improvement in the American College of Rheumatology core set disease index after 24 weeks of treatment.

In some embodiments, as a result of the treatment, the subject achieves a lower disease activity score after 12 weeks of treatment than the subject had before treatment. The disease activity score can be less than or equal to 2.6 at 12 weeks. The disease activity score can decrease by greater than 1.2 between start of treatment and 12 weeks. The disease activity score can be less than or equal to 3.2 at 12 weeks. The disease activity score can decrease by greater than 0.6 between start of treatment and 12 weeks. The disease activity score can be less than or equal to 5.1 at 12 weeks.

In some embodiments, as a result of the treatment, the subject achieves a lower disease activity score after 24 weeks of treatment than the subject had before treatment. The disease activity score can be less than or equal to 2.6 at 24 weeks. The disease activity score can decrease by greater than 1.2 between start of treatment and 24 weeks. The disease activity score can be less than or equal to 3.2 at 24 weeks. The disease activity score can decrease by greater than 0.6 between start of treatment and 24 weeks. The disease activity score can be less than or equal to 5.1 at 24 weeks.

The present disclosure also provides a method of treating rheumatoid arthritis in a subject in need thereof comprising administering to the subject an effective amount of sarilumab and methotrexate, wherein the subject was previously ineffectively treated for rheumatoid arthritis by administering an anti-TNF-α therapeutic. In certain embodiments, the subject was previously ineffectively treated for rheumatoid arthritis by administering methotrexate. The methotrexate can be administered at between 10 to 25 mg per week to the subject.

In certain embodiments, the subject is a mammal. The mammal can be a human. In certain embodiments, the human is descended from individuals from Asia or the Pacific. Humans descended from individuals from Asia or the Pacific can be administered between 6 and 25 mg per week of methotrexate.

In certain embodiments, the subject was previously ineffectively treated for rheumatoid arthritis by administering a TNF-α antagonist. Specifically, subject could have been treated for at least three months with the TNF-α antagonist or could have been intolerant of the TNF-α antagonist. The TNF-α antagonist could be etanercept, infliximab, adalimumab, golimumab or certolizumab. In other embodiments, the subject was previously ineffectively treated for rheumatoid arthritis by administering methotrexate.

The sarilumab could be administered at between 50 and 150 mg per week or between 100 and 200 mg per two weeks.

In some embodiments, as a result of the treatment, the subject achieves a 20% or 50% improvement in the American College of Rheumatology core set disease index after 12 weeks of treatment. In other embodiments, as a result of the treatment, the subject achieves a 20%, 50% or 70% improvement in the American College of Rheumatology core set disease index after 24 weeks of treatment.

In some embodiments, as a result of the treatment, the subject achieves a lower disease activity score after 12 weeks of treatment than the subject had before treatment. The disease activity score can be less than or equal to 2.6 at 12 weeks. The disease activity score can decrease by greater than 1.2 between start of treatment and 12 weeks. The disease activity score can be less than or equal to 3.2 at 12 weeks. The disease activity score can decrease by greater than 0.6 between start of treatment and 12 weeks. The disease activity score can be less than or equal to 5.1 at 12 weeks.

In some embodiments, as a result of the treatment, the subject achieves a lower disease activity score after 24 weeks of treatment than the subject had before treatment. The disease activity score can be less than or equal to 2.6 at 24 weeks. The disease activity score can decrease by greater than 1.2 between start of treatment and 24 weeks. The disease activity score can be less than or equal to 3.2 at 24 weeks. The disease activity score can decrease by greater than 0.6 between start of treatment and 24 weeks. The disease activity score can be less than or equal to 5.1 at 24 weeks.

The disclosure also provides a pharmaceutical composition comprising an effective amount of sarilumab and a member of the group consisting of leflunomide, sulfasalazine and hydroxychloroquine. The sarilumab could be present at between 50 and 150 mg per dose or between 100 and 200 mg per dose.

In certain specific embodiments, the composition includes sarilumab and leflunomide. The leflunomide can be present in an oral dosage form. The leflunomide can be present in the composition at between 10 and 20 mg per dose.

In other specific embodiments, the composition includes sarilumab and sulfasalazine. The sulfasalazine can be present in an oral dosage form. The sulfasalazine can be present in the composition at between 1000 to 3000 mg per day to the subject.

In other specific embodiments, the composition includes sarilumab and hydroxychloroquine. The hydroxychloroquine can be present in an oral dosage form. The hydroxychloroquine can be present in the composition at between 200 to 400 mg per day to the subject.

Examples of embodiments of the invention are listed below:

- Embodiment 1: A method of treating rheumatoid arthritis in a subject in need thereof comprising administering to the subject an effective amount of sarilumab (SAR153191) and a member of the group consisting of leflunomide, sulfasalazine and hydroxychloroquine.
- Embodiment 2: The method of embodiment 1, wherein the subject was previously ineffectively treated for rheumatoid arthritis by administering a TNF-α antagonist.
- Embodiment 3: The method of embodiment 2, wherein the TNF-α antagonist is a biologic anti-TNF-α antagonist.
- Embodiment 4: The method of embodiment 2 or 3, wherein the subject was treated for at least three months with the TNF-α antagonist.
- Embodiment 5: The method of embodiment 2 or 3, wherein the subject was intolerant of the TNF-α antagonist.
- Embodiment 6: The method of embodiment 2 or 3, wherein the TNF-α antagonist is selected from the group consisting of etanercept, infliximab, adalimumab, golimumab and certolizumab.
- Embodiment 7: The method of embodiment 2 or 3, wherein the subject was previously ineffectively treated for rheumatoid arthritis by administering methotrexate.
- Embodiment 8: The method of embodiment 1, wherein the sarilumab is administered at between 50 and 150 mg per week.
- Embodiment 9: The method of embodiment 1, wherein the sarilumab is administered at between 100 and 200 mg per two weeks.
- Embodiment 10: The method of embodiment 1, wherein sarilumab and leflunomide are administered to the subject.
- Embodiment 11: The method of embodiment 10, wherein the leflunomide is administered orally.
- Embodiment 12: The method of embodiment 10, wherein the leflunomide is administered at between 10 and 20 mg per day to the subject.
- Embodiment 13: The method of embodiment 1, wherein sarilumab and sulfasalazine are administered to the subject.
- Embodiment 14: The method of embodiment 13, wherein the sulfasalazine is administered orally.
- Embodiment 15: The method of embodiment 13, wherein the sulfasalazine is administered at between 1000 to 3000 mg per day to the subject.
- Embodiment 16: The method of embodiment 1, wherein sarilumab and hydroxychloroquine are administered to the subject.
- Embodiment 17: The method of embodiment 16, wherein the hydroxychloroquine is administered orally.
- Embodiment 18: The method of embodiment 16, wherein the hydroxychloroquine is administered at between 200 to 400 mg per day to the subject.
- Embodiment 19: The method of any of embodiments 1-18, wherein the subject achieves a 20% improvement in the American College of Rheumatology core set disease index after 12 weeks of treatment.
- Embodiment 20: The method of any of embodiments 1-18, wherein the subject achieves a 50% improvement in the American College of Rheumatology core set disease index after 12 weeks of treatment.
- Embodiment 21: The method of any of embodiments 1-18, wherein the subject achieves a 20% improvement in the American College of Rheumatology core set disease index after 24 weeks of treatment.
- Embodiment 22: The method of any of embodiments 1-18, wherein the subject achieves a 50% improvement in the American College of Rheumatology core set disease index after 24 weeks of treatment.

Embodiment 23: The method of any of embodiments 1-18, wherein the subject achieves a 70% improvement in the American College of Rheumatology core set disease index after 24 weeks of treatment.

Embodiment 24: The method of any of embodiments 1-18, wherein the subject achieves a lower disease activity score after 12 weeks of treatment than the subject had before treatment.

Embodiment 25: The method of any of embodiments 1-18, wherein the disease activity score is less than or equal to 2.6 at 12 weeks.

Embodiment 26: The method of any of embodiments 1-18, wherein the disease activity score decreases by greater than 1.2 between start of treatment and 12 weeks.

Embodiment 27: The method of any of embodiments 1-18, wherein the disease activity score is less than or equal to 3.2 at 12 weeks.

Embodiment 28: The method of any of embodiments 1-18, wherein the disease activity score decreases by greater than 0.6 between start of treatment and 12 weeks.

Embodiment 29: The method of any of embodiments 1-18, wherein the disease activity score is less than or equal to 5.1 at 12 weeks.

Embodiment 30: The method of any of embodiments 1-18, wherein the subject achieves a lower disease activity score after 24 weeks of treatment than the subject had before treatment.

Embodiment 31: The method of any of embodiments 1-18, wherein the disease activity score is less than or equal to 2.6 at 24 weeks.

Embodiment 32: The method of any of embodiments 1-18, wherein the disease activity score decreases by greater than 1.2 between start of treatment and 24 weeks.

Embodiment 33: The method of any of embodiments 1-18, wherein the disease activity score is less than or equal to 3.2 at 24 weeks.

Embodiment 34: The method of any of embodiments 1-18, wherein the disease activity score decreases by greater than 0.6 between start of treatment and 24 weeks.

Embodiment 35: The method of any of embodiments 1-18, wherein the disease activity score is less than or equal to 5.1 at 24 weeks.

Embodiment 36: A method of treating rheumatoid arthritis in a subject in need thereof comprising administering to the subject an effective amount of sarilumab and methotrexate, wherein the subject was previously ineffectively treated for rheumatoid arthritis by administering an anti-TNF-α antagonist.

Embodiment 37: The method of embodiment 36, wherein the subject was previously ineffectively treated for rheumatoid arthritis by administering methotrexate.

Embodiment 38: The method of embodiment 36, wherein the methotrexate is administered at between 10 to 25 mg per week to the subject.

Embodiment 39: The method of embodiment 36, wherein the subject is a mammal.

Embodiment 40: The method of embodiment 37, wherein the mammal is a human.

Embodiment 41: The method of embodiment 38, wherein the human is descended from individuals from Asia or the Pacific.

Embodiment 42: The method of embodiment 39, wherein the humans descended from individuals from Asia or the Pacific are administered between 6 and 25 mg per week of methotrexate.

Embodiment 43: The method of embodiment 36, wherein the subject was treated for at least three months with the TNF-α antagonist.

Embodiment 44: The method of embodiment 36, wherein the subject was intolerant of the TNF-α antagonist.

Embodiment 45: The method of embodiment any one of embodiments 36-44, wherein the TNF-α antagonist is a biologic anti-TNF-α antagonist.

Embodiment 46: The method of embodiment 44, wherein the TNF-α antagonist is selected from the group consisting of etanercept, infliximab, adalimumab, golimumab and certolizumab.

Embodiment 47: The method of embodiment 36, wherein the sarilumab is administered at between 50 and 150 mg per week.

Embodiment 48: The method of embodiment 36, wherein the sarilumab is administered at between 100 and 200 mg per two weeks.

Embodiment 49: The method of any of embodiments 36-48, wherein the subject achieves a 20% improvement in the American College of Rheumatology core set disease index after 12 weeks of treatment.

Embodiment 50: The method of any of embodiments 36-48, wherein the subject achieves a 50% improvement in the American College of Rheumatology core set disease index after 12 weeks of treatment.

Embodiment 51: The method of any of embodiments 36-48, wherein the subject achieves a 20% improvement in the American College of Rheumatology core set disease index after 24 weeks of treatment.

Embodiment 52: The method of any of embodiments 36-48, wherein the subject achieves a 50% improvement in the American College of Rheumatology core set disease index after 24 weeks of treatment.

Embodiment 53: The method of any of embodiments 36-48, wherein the subject achieves a 70% improvement in the American College of Rheumatology core set disease index after 24 weeks of treatment.

Embodiment 54: The method of any of embodiments 36-48, wherein the subject achieves a lower disease activity score after 12 weeks of treatment than the subject had before treatment.

Embodiment 55: The method of any of embodiments 36-48, wherein the disease activity score is less than or equal to 2.6 at 12 weeks.

Embodiment 56: The method of any of embodiments 36-48, wherein the disease activity score decreases by greater than 1.2 between start of treatment and 12 weeks.

Embodiment 57: The method of any of embodiments 36-48, wherein the disease activity score is less than or equal to 3.2 at 12 weeks.

Embodiment 58: The method of any of embodiments 36-48, wherein the disease activity score decreases by greater than 0.6 between start of treatment and 12 weeks.

Embodiment 59: The method of any of embodiments 36-48, wherein the disease activity score is less than or equal to 5.1 at 12 weeks.

Embodiment 60: The method of any of embodiments 36-48, wherein the subject achieves a lower disease activity score after 24 weeks of treatment than the subject had before treatment.

Embodiment 61: The method of any of embodiments 36-48, wherein the disease activity score is less than or equal to 2.6 at 24 weeks.

Embodiment 62: The method of any of embodiments 36-48, wherein the disease activity score decreases by greater than 1.2 between start of treatment and 24 weeks.

Embodiment 63: The method of any of embodiments 34-45, wherein the disease activity score is less than or equal to 3.2 at 24 weeks.

Embodiment 64: The method of any of embodiments 34-45, wherein the disease activity score decreases by greater than 0.6 between start of treatment and 24 weeks.

Embodiment 65: The method of any of embodiments 34-45, wherein the disease activity score is less than or equal to 5.1 at 24 weeks.

Embodiment 66: A pharmaceutical composition comprising an effective amount of sarilumab and a member of the group consisting of leflunomide, sulfasalazine and hydroxychloroquine.

DETAILED DESCRIPTION

Figure 1:
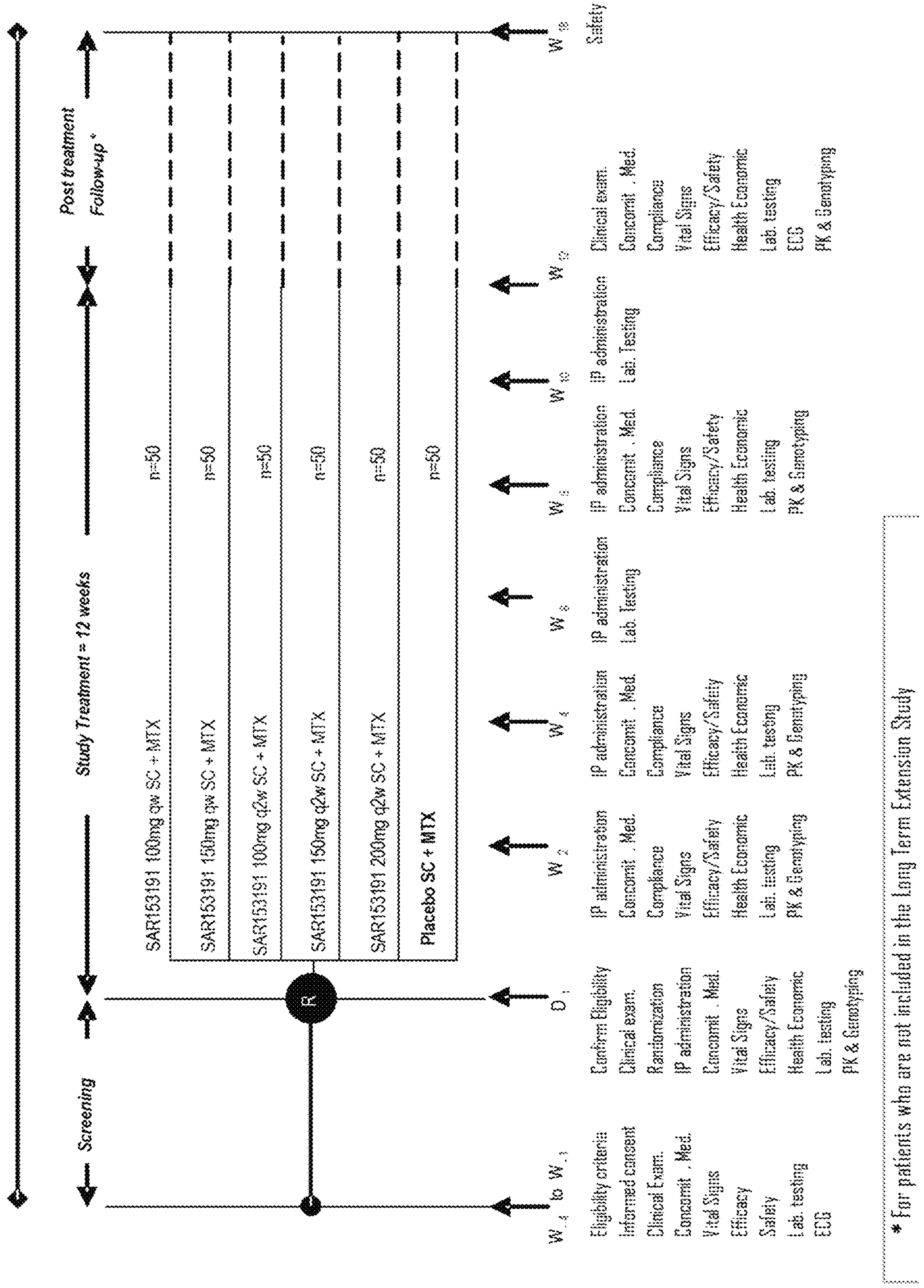
FIG. 1 depicts the study design for an international multi-center, double-blind, parallel group placebo-controlled, 12-week study treatment of six arms of SAR153191 or placebo given subcutaneously weekly with methotrexate (MTX) co-therapy.

The disclosure provides pharmaceutical compositions and methods of using these compositions for the treatment of rheumatoid arthritis (RA) and the improvement of at least one symptom of RA. These compositions include at least one antibody that specifically binds human interleukin-6 receptor (hIL-6R) and at least one disease modifying anti-rheumatic drug (DMARD).

Anti-hIL-6R Antibodies

The present disclosure includes methods that comprise administering to a patient a human antibody, or an antigen-binding fragment thereof, that binds specifically to hIL-6R. As used herein, the term "hIL-6R" means a human cytokine receptor that specifically binds human interleukin-6 (IL-6). In certain embodiments, the antibody that is administered to the patient binds specifically to the extracellular domain of hIL-6R. The extracellular domain of hIL-6R is shown in the amino acid sequence of SEQ ID NO: 1.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab') 2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_{H1}$; (ii) $V_H$-$C_{H2}$; (iii) $V_H$-$C_{H3}$; (IV) $V_H$-$C_{H1}$-$C_{H2}$; (V) $V_H$-$C_{H1}$-$C_{H2}$-$C_{H3}$; (Vi) $V_H$-$C_{H2}$-$C_{H3}$; (Vii) $V_H$-$C_L$; (viii) $V_L$-$C_{H1}$; (ix) $V_L$-$C_{H2}$; (x) $V_L$-$C_{H3}$; (xI) $V_L$-$C_{H1}$-$C_{H2}$; (xii) $V_L$-$C_{H1}$-$C_{H2}$-$C_{H3}$; (xiii) $V_L$-$C_{H2}$-$C_{H3}$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "specifically binds," means that an antibody or antigen-binding fragment thereof forms a complex with an antigen that is relatively stable under physiologic conditions. Specific binding can be characterized by a dissociation constant of at least about $1\times10^{-6}$ M or smaller. In other embodiments, the dissociation constant is at least about $1\times10^{-7}$ M, $1\times10^{-8}$ M, or $1\times10^{-9}$ M. Methods for determining whether two molecules specifically bind are well known in the art and include, for example, equilibrium dialysis, surface plasmon resonance, and the like.

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In specific embodiments, the antibody or antibody fragment for use in the method of the invention may be a multispecific antibody, which may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_{H3}$ domain and a second Ig $C_{H3}$ domain, wherein the first and second Ig $C_{H3}$ domains differ from one another by at least one amino acid, and wherein at least one amino acid difference reduces binding of the bispecific antibody to Protein A as compared to a bi-specific antibody lacking the amino acid difference. In one embodiment, the first Ig $C_{H3}$ domain binds Protein A and the second Ig $C_{H3}$ domain contains a mutation that reduces or abolishes Protein A binding such as an H95R modification (by IMGT exon numbering; H435R by EU numbering). The second $C_{H3}$ may further comprise an Y96F modification (by IMGT; Y436F by EU). Further modifications that may be found within the second $C_{H3}$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

In other specific embodiments, the antibody is sarilumab (SAR153191). The heavy chain variable region of sarilumab is shown below as SEQ ID NO:2.

The light chain variable region of sarilumab is shown below as SEQ ID NO:3. A "neutralizing" or "blocking" antibody, as used herein, is intended to refer to an antibody whose binding to hIL-6R results in inhibition of the biological activity of hIL-6. This inhibition of the biological activity of hIL-6 can be assessed by measuring one or more indicators of hIL-6 biological activity known to the art, such as hIL-6-induced cellular activation and hIL-6 binding to hIL-6R (see examples below).

The fully-human anti-IL-6R antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, the antibodies of the present invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The term "epitope" refers to an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sufonyl groups on the antigen.

The anti-hIL-6R can be sarilumab (SAR153191). In one embodiment, sarilumab is defined as an antibody comprising the heavy chain variable region of SEQ ID NO:2 and the light chain variable region of SEQ ID NO:3.

DMARDs

Disease modifying antirheumatic drugs (DMARDs) include methotrexate, sulfasalazine, hydroxychloroquine and leflunomide. According to the compositions and methods of the disclosure, DMARDs can be administered as follows. Methotrexate can be administered from 10 to 25 mg per week orally or intramuscularly. In another embodiment, methotrexate is administered from 6 to 25 mg/week orally or intramuscularly for patients who are from the Asia-Pacific region or who are descended from people who are from the Asia-Pacific region. The Asia-Pacific region includes Taiwan, South Korea, Malaysia, Philippines, Thailand and India. In certain embodiments, methotrexate is administered at between 6 and 12, 10 and 15, 15 and 20 and 20 and 25 mg per week. In other embodiments, methotrexate is administered at 6, 7, 8, 9, 10, 11, 12, 13, 14, 15, 16, 17, 18, 19, 20, 21, 22, 23, 24 or 25 mg per week. Leflunomide can be administered from 10 to 20 mg orally daily. In certain embodiments, leflunomide can be administered at between 10 and 12, 12 and 15, 15 and 17 and 18 and 20 mg per day. In other embodiments, leflunomide is administered at 10, 11, 12, 13, 14, 15, 16, 17, 18, 19 or 20 mg per day. Sulfasalazine can be administered from 1000 to 3000 mg orally daily. In certain embodiments, sulfasalazine can be administered at between 1000 and 1400, 1400 and 1800, 1800 and 2200, 2200 and 2600, and 2600 and 3000 mg per day. In other embodiments, sulfasalazine is administered at 1000, 1100, 1200, 1300, 1400, 1500, 1600, 1700, 1800, 1900, 2000, 2100, 2200, 2300, 2400, 2500, 2600, 2700, 2800, 2900 or 3000 mg per day. Hydroxychloroquine can be administered from 200 to 400 mg orally daily. In certain embodiments, hydroxychloroquine can be administered at between 200 and 240, 240 and 280, 280 and 320, 320 and 360 and 360 and 400 per day. In other embodiments, hydroxychloroquine can be administered at 200, 210, 220, 230, 240, 250, 260, 270, 280, 290, 300, 310, 320, 330, 340, 350, 360, 370, 380, 390 or 400 mg per day.

Therapeutic Administration and Formulations

The methods described herein comprise administering a therapeutically effective amount of an anti-hIL-6R antibody and a DMARD to a patient. As used herein, the phrase "therapeutically effective amount" means a dose of anti-hIL-6R antibody and a DMARD that results in a detectable improvement in one or more symptoms associated with rheumatoid arthritis or which causes a biological effect (e.g., a decrease in the level of a particular biomarker) that is correlated with the underlying pathologic mechanism(s) giving rise to the condition or symptom(s) of rheumatoid arthritis. For example, a dose of anti-hIL-6R antibody with one or more DMARDs which causes an improvement in any of the following symptoms or conditions is deemed a "therapeutically effective amount": chronic disease anemia, fever, depression, fatigue, rheumatoid nodules, vasculitis, neuropathy, scleritis, pericarditis, Felty's syndrome and/or joint destruction.

A detectable improvement can also be detected using the American College of Rheumatism (ACR) rheumatoid arthritis classification criteria. For example a 20% (ACR20), 50% (ACR50) or 70% (ACR70) improvement from baseline can be used to show detectable improvement.

The disease activity score (DAS28) can be used to show detectable improvement. DAS28 is a composite score of tender joints count based on 28 joints, a swollen joints count based on 28 joints, a general health assessment and a marker of inflammation which can be assessed by measuring C-reactive protein (CRP) levels. The disease response can be presented using the European League against Rheumatism (EULAR) response criteria. A good response by this criteria is an improvement of greater than 1.2 in DAS28 score with a present score of greater than or equal to 3.2. A moderate response is an improvement of greater than 0.6 but less than or equal to 1.2 in DAS28 score and a present score of greater than 3.2. Non-response is an improvement of less than 0.6 in DAS28 score and a present score of greater than 5.1. DAS28 remission is a DAS28 score of less than 2.6.

In accordance with the methods of the present invention, a therapeutically effective amount of anti-hIL-6R antibody that is administered to the patient will vary depending upon the age and the size (e.g., body weight or body surface area) of the patient as well as the route of administration and other factors well known to those of ordinary skill in the art. In certain embodiments, the dose of anti-hIL-6R antibody administered to the patient is from about 10 mg to about 500 mg. For example, the present invention includes methods wherein about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300, about 325 mg, about 350 mg, about 375 mg, about 400 mg, about 425 mg, about 450 mg, about 475 mg, about 500 mg, or more of anti-hIL-6R antibody is administered to the patient per week.

In one embodiment, the hIL-6R antibody is administered at 100-150 mg per week. In another embodiment, the hIL-6R antibody is administered at 100-200 mg per ever two weeks. In other embodiments, the hIL-6R antibody is administered at about 100 or about 150 mg per week. In other embodiments, the hIL-6R antibody is administered at about 100, 150 or 200 mg per every two weeks.

The amount of anti-hIL-6R antibody that is administered to the patient may be expressed in terms of milligrams of antibody per kilogram of patient body weight (i.e., mg/kg). For example, the methods of the present invention include administering an anti-hIL-6R antibody to a patient at a daily dose of about 0.01 to about 100 mg/kg, about 0.1 to about 50 mg/kg, or about 1 to about 10 mg/kg of patient body weight.

The methods of the present invention include administering multiple doses of an anti-hIL-6R antibody to a patient over a specified time course. For example, the anti-hIL-6R antibody can be administered about 1 to 5 times per day, about 1 to 5 times per week, about 1 to 5 times per month or about 1 to 5 times per year. In certain embodiments, the methods of the invention include administering a first dose of anti-hIL-6R antibody to a patient at a first time point, followed by administering at least a second dose of anti-hIL-6R antibody to the patient at a second time point. The first and second doses, in certain embodiments, may contain the same amount of anti-hIL-6R antibody. For instance, the first and second doses may each contain about 10 mg to about 500 mg, about 20 mg to about 300 mg, about 100 mg to about 200 mg, or about 100 mg to about 150 mg of the antibody. The time between the first and second doses may be from about a few hours to several weeks. For example, the second time point (i.e., the time when the second dose is administered) can be from about 1 hour to about 7 weeks after the first time point (i.e., the time when the first dose is administered). According to certain exemplary embodiments of the present invention, the second time point can be about 1 hour, about 4 hours, about 6 hours, about 8 hours, about 10 hours, about 12 hours, about 24 hours, about 2 days, about 3 days, about 4 days, about 5 days, about 6 days, about 7 days, about 2 weeks, about 4 weeks, about 6 weeks, about 8 weeks, about 10 weeks, about 12 weeks, about 14 weeks or longer after the first time point. In certain embodiments, the second time point is about 1 week or about 2 weeks. Third and subsequent doses may be similarly administered throughout the course of treatment of the patient.

The invention provides methods of using therapeutic compositions comprising anti-IL-6R antibodies or antigen-binding fragments thereof and one or more DMARDs. The therapeutic compositions of the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the weight of a subject to be administered, target disease, conditions, route of administration, and the like. Various delivery systems are known and can be used to administer the pharmaceutical composition of the invention, e.g., encapsulation in liposomes, microparticles, microcapsules, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The hIL-6R antibody can be administered subcutaneously. The DMARD can be administered orally or intramuscularly.

The pharmaceutical composition can also be delivered in a vesicle, in particular a liposome (see Langer (1990) Science 249:1527-1533). In certain situations, the pharmaceutical composition can be delivered in a controlled release system, for example, with the use of a pump or polymeric materials. In another embodiment, a controlled release system can be placed in proximity of the composition's target, thus requiring only a fraction of the systemic dose.

The injectable preparations may include dosage forms for intravenous, subcutaneous, intracutaneous and intramuscular injections, local injection, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the DMARD contained is generally about 5 to 3000 mg per dosage form in an oral unit dose depending on the specific DMARD used. The amount of the hIL-6R antibody contained is generally about 100 to 200 mg per subcutaneous dosage form.

In accordance with the methods disclosed herein, the anti-hIL-6R antibody (or pharmaceutical formulation comprising the antibody) can be administered to the patient using any acceptable device or mechanism. For example, the administration can be accomplished using a syringe and needle or with a reusable pen and/or autoinjector delivery device. The methods of the present invention include the use of numerous reusable pen and/or autoinjector delivery devices to administer an anti-hIL-6R antibody (or pharmaceutical formulation comprising the antibody). Examples of such devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™ and OPTICLIK™ (sanofi-aventis, Frankfurt, Germany), to name only a few. Examples of disposable pen and/or autoinjector delivery devices having applications in subcutaneous delivery of a pharmaceutical composition of the present invention include, but are not limited to the SOLOSTART pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.), and the HUMIRA™ Pen (Abbott Labs, Abbott Park, IL), to name only a few.

The use of a microinfusor to deliver an anti-hIL-6R antibody (or pharmaceutical formulation comprising the antibody) to a patient is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., J. Controlled Release 46:107-116 (1996). Microinfusors are particularly useful for the delivery of large doses of therapeutic proteins contained within high concentration (e.g., about 100, 125, 150, 175, 200 or more mg/mL) and/or viscous solutions.

Combination Therapies

The present invention includes methods of treating rheumatoid arthritis which comprise administering to a patient in need of such treatment an anti-hIL-6R antibody in combination with at least one additional therapeutic agent. Examples of additional therapeutic agents which can be administered in combination with an anti-hIL-6R antibody in the practice of the methods of the present invention include, but are not limited to DMARDs, and any other compound known to treat, prevent, or ameliorate rheumatoid arthritis in a human subject. Specific, non-limiting examples of additional therapeutic agents that may be administered in combination with an anti-hIL-6R antibody in the context of a method of the present invention include, but are not limited to methotrexate, sulfasalazine, hydroxychloroquine and leflunomide. In the present methods, the additional therapeutic agent(s) can be administered concurrently or sequentially with the anti-hIL-6R antibody. For example, for concurrent administration, a pharmaceutical formulation can be made which contains both an anti-hIL-6R antibody and at least one additional therapeutic agent. The amount of the additional therapeutic agent that is administered in combination with the anti-hIL-6R antibody in the practice of the methods of the present invention can be easily determined using routine methods known and readily available in the art.

The disclosure of the invention provides for pharmaceutical compositions comprising any of the following:

A composition comprising between 100 and 150 mg of sarilumab (SAR153191) and 10-25 mg of methotrexate.

A composition comprising between 100 and 200 mg of sarilumab (SAR153191) and 10-25 mg of methotrexate.

A composition comprising between 100 and 150 mg of sarilumab (SAR153191) and 6-25 mg of methotrexate.

A composition comprising between 100 and 200 mg of sarilumab (SAR153191) and 6-25 mg of methotrexate.

A composition comprising between 100 and 150 mg of sarilumab (SAR153191) and 10-20 mg of leflunomide.

A composition comprising between 100 and 200 mg of sarilumab (SAR153191) and 10-20 mg of leflunomide.

A composition comprising between 100 and 150 mg of sarilumab (SAR153191) and 1000-3000 mg of sulfasalazine.

A composition comprising between 100 and 200 mg of sarilumab (SAR153191) and 1000-3000 mg of sulfasalazine.

A composition comprising between 100 and 150 mg of sarilumab (SAR153191) and 200-400 mg of hydroxychloroquine.

A composition comprising between 100 and 200 mg of sarilumab (SAR153191) and 200-400 mg of hydroxychloroquine.

The disclosure of the invention provides for methods of improving symptoms associated with rheumatoid arthritis comprising any of the following:

A method comprising administering between 100 and 150 mg of sarilumab (SAR153191) and 10-25 mg of methotrexate per week to a subject in need thereof. A method comprising administering between 100 and 200 mg of sarilumab (SAR153191) every two weeks and 10-25 mg of methotrexate per week to a subject in need thereof.

A method comprising administering between 100 and 150 mg of sarilumab (SAR153191) and 6-25 mg of methotrexate per week to a subject in need thereof. A method comprising administering between 100 and 200 mg of sarilumab (SAR153191) every two weeks and 6-25 mg of methotrexate per week to a subject in need thereof.

A method comprising administering between 100 and 150 mg of sarilumab (SAR153191) per week and 10-20 mg of leflunomide per day to a subject in need thereof.

A method comprising administering between 100 and 200 mg of sarilumab (SAR153191) every two weeks and 10-20 mg of leflunomide per day to a subject in need thereof.

A method comprising administering between 100 and 150 mg of sarilumab (SAR153191) per week and 1000-3000 mg of sulfasalazine per day to a subject in need thereof.

A method comprising administering between 100 and 200 mg of sarilumab (SAR153191) every two weeks and 1000-3000 mg of sulfasalazine per day to a subject in need thereof.

A method comprising administering between 100 and 150 mg of sarilumab (SAR153191) per week and 200-400 mg of hydroxychloroquine per day to a subject in need thereof.

A method comprising administering between 100 and 200 mg of sarilumab (SAR153191) every two weeks and 200-400 mg of hydroxychloroquine per day to a subject in need thereof.

Biomarkers

The present disclosure includes methods of treating rheumatoid arthritis by administering to a patient in need of such treatment a therapeutically effective amount of a human antibody or antibody binding fragment thereof which specifically binds to hIL-6R and a therapeutically effective amount of one or more DMARDs, wherein the level of one or more RA-associated biomarkers in the patient is modified (e.g., increased, decreased, etc., as the case may be) following administration. In a related aspect, the present invention includes methods for decreasing an RA-associated biomarker in a patient by administering to the patient a therapeutically-effective amount of a human antibody or antigen-binding fragment thereof which specifically binds to hIL-6R and a therapeutically effective amount of one or more DMARDs.

Examples of RA-associated biomarkers include, but are not limited to, e.g., high-sensitivity C-reactive protein (hsCRP), serum amyloid A (SAA), erythrocyte sedimentation rate (ESR), serum hepcidin, interleukin-6 (IL-6), and hemoglobin (Hb). As will be appreciated by a person of ordinary skill in the art, an increase or decrease in an RA-associated biomarker can be determined by comparing the level of the biomarker measured in the patient at a defined time point after administration of the anti-IL-6R antibody to the level of the biomarker measured in the patient prior to the administration (i.e., the "baseline measurement"). The defined time point at which the biomarker can be measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days or more after administration of the anti-hIL-6R antibody.

According to certain embodiments of the present invention, a patient may exhibit a decrease in the level of one or more of hsCRP, SAA, ESR and/or hepcidin following administration of an anti-hIL-6R antibody to the patient. For example, at about week 12 following weekly administration of anti-hIL-6R antibody and one or more DMARDs the patient may exhibit one or more of the following: (i) a decrease in hsCRP by about 40%, 45%, 50%, 55%, 60%, 65%, 70%, 75%, 80%, 85%, 90%, 95% or more; (ii) a decrease in SAA by about 40%, 45%, 50%, 55%, 60%, 65%, 70%, 75%, 80%, 85%, 90%, 95% or more; (iii) a decrease in ESR by about 15%, 20%, 25%, 30%, 35%, 40%, 45%, 50%, 55% or more; and/or (iv) a decrease in hepcidin by about 30%, 35%, 40%, 45%, 50%, 55%, 60%, 65%, 70%, 75% or more.

According to certain other embodiments of the present invention, a patient may exhibit an increase in the level of one or more of Hb or IL-6 following administration of an anti-hIL-6R antibody and one or more DMARDs to the patient. For example, at about week 12 following weekly administration of anti-hIL-6R antibody and one or more DMARDs the patient may exhibit one or more of the following: (v) an increase in Hb by about 0.5%, 1.0%, 1.5%, 2.0%, 2.5%, 3.0%, 3.5%, 4.0%, 4.5%, 5.0%, 5.5%, 6.0% or more; and/or (vi) an increase in IL-6 by about 100%, 150%, 200%, 250%, 300%, 350%, 400%, 450%, 500%, 550%, 600%, 650%, 700%, 750%, 800% or more.

The present invention includes methods for determining whether a subject is a suitable patient for whom administration of an anti-hIL-6R antibody would be beneficial. For example, if an individual, prior to receiving an anti-hIL-6R antibody and/or one or more DMARDs, exhibits a level of an RA-associated biomarker which signifies the disease state, the individual is therefore identified as a suitable patient for whom administration of an anti-hIL-6R antibody would be beneficial. According to certain exemplary embodiments, an individual may be identified as a good candidate for anti-hIL-6R/DMARD therapy if the individual exhibits one or more of the following: (i) a level of hsCRP greater than about 4 mg/L (e.g., about 4.5 mg/L, about 5.0 mg/L, about 5.5 mg/L, about 6.0 mg/L, about 7.0 mg/L, about 10.0 mg/L, about 15.0 mg/L, about 20.0 mg/L, or more); (ii) a level of SAA greater than about 3800 ng/ml (e.g., about 4000 ng/ml, 4500 ng/ml, about 5000 ng/mL, about 5500 ng/ml, about 6000 ng/ml, about 10,000 ng/ml, about 20,000 ng/ml, about 25,000 ng/ml, about 30,000 ng/ml, about 35,000 ng/ml, about 40,000 ng/ml, about 45,000 ng/ml, or more); (iii) an ESR greater than about 15 mm/hr (e.g., about 16 mm/hr, about 17 mm/hr, about 18 mm/hr, about 19 mm/hr, about 20 mm/hr, about 21 mm/hr, about 22 mm/hr, about 25 mm/hr, about 30 mm/hr, about 35 mm/hr, about 40 mm/hr, about 45 mm/hr, about 50 mm/hr, or more); and/or (iv) a level of hepcidin greater than about 60 ng/ml (e.g., about 62 ng/ml, about 64 ng/ml, about 68 ng/mL, about 70 ng/ml, about 72 ng/ml, about 74 ng/ml, about 76 ng/ml, about 78 ng/mL, about 80 ng/ml, about 82 ng/ml, about 84 ng/ml, about 85 ng/ml, about 90 ng/ml, about 95 ng/ml, about 100 ng/ml, about 105 ng/ml, or more). Additional criteria, such as other clinical indicators of RA, may be used in combination with any of the foregoing RA-associated biomarkers to identify an individual as a suitable candidate for anti-hIL-6R therapy.

Patient Population

In certain embodiments, the methods and compositions described herein are administered to specific patient populations. These populations include patients that have previously been treated for rheumatoid arthritis with treatment regimens other than the combination of an anti-hIL-6R antibody and one or more DMARDs. These treatment regimens include anti-TNF-α therapy, e.g., biologic anti-TNF-α treatment regimens. Biologic anti-TNF-α antagonists include etanercept, infliximab, adalimumab, golimumab and certolizumab pegol. These treatment regimens also include DMARD therapy in the absence of anti-hIL-6R antibody.

DMARDs used in this therapy include methotrexate, sulfasalazine, hydroxychloroquine and leflunomide. The DMARDs may be administered alone or in combination with another therapy that is not an anti-hIL-6R antibody. In a specific embodiment, the previous treatment regimen was methotrexate. In another embodiment, treatment with methotrexate is maintained in patient treated with an anti-hIL-6R antibody. In certain embodiments, the patient has previously been administered both anti-TNF-α and DMARD therapies. The therapies may be performed sequentially in any order or simultaneously. In certain embodiments, these therapies have been received by the patient within 2 years prior to receiving the combination of an anti-hIL-6R antibody and one or more DMARDs. In other embodiments, these therapies have been received within 1, 2, 3, 4, 5, 6, 7, 8, 9 or 10 years prior to receiving the combination of an anti-hIL-6R antibody and one or more DMARDs.

In certain embodiments, the methods and compositions described herein are administered to specific patient populations that have received one or more of the treatment regimens described above wherein these treatments have not been effective. As used herein, a treatment has not been effective when a dose of anti-TNF-α and a DMARD do not result in a detectable improvement in one or more symptoms associated with rheumatoid arthritis or do not cause a biological effect (e.g., a decrease in the level of a particular biomarker) that is correlated with the underlying pathologic mechanism(s) giving rise to the condition or symptom(s) of rheumatoid arthritis.

In another example, a treatment has not been effective when a dose of anti-TNF-α does not result in a detectable improvement in one or more symptoms associated with rheumatoid arthritis or does not cause a biological effect (e.g., a decrease in the level of a particular biomarker) that is correlated with the underlying pathologic mechanism(s) giving rise to the condition or symptom(s)

In another example, a treatment has not been effective when a dose of anti-hIL-6R antibody and a DMARD that does not result in a detectable improvement in one or more symptoms associated with rheumatoid arthritis or which does not cause a biological effect that is correlated with the underlying pathologic mechanism(s) giving rise to the condition or symptom(s) of rheumatoid arthritis.

In certain embodiment, sarilumab is administered to a patient who has previously been inefficiently treated with a DMARD. As used herein, a treatment with a DMARD has not been effective when a patient still presents an "active disease" after treatment. Patients present an active disease when they exhibit at least 8 of 68 tender joints and 6 of 66 swollen joints, and high sensitivity C-reactive protein (hs-CRP)>10 mg/L (>1.0 mg/dL). In a specific embodiment, patients have previously been inefficiently treated with MTX. In such example, patients may have received continuous treatment with MTX 10 to 25 mg/week (or per local labeling requirements if the dose range differs) for at least 12 weeks and on a stable dose of MTX for a minimum of 8 weeks and still present a moderate-to-severely active RA, defined as: (i) at least 8 of 68 tender joints and 6 of 66 swollen joints, and (ii) high sensitivity C-reactive protein (hs-CRP)>10 mg/L (>1.0 mg/dL).

For example, a treatment which does not cause an improvement in any of the following symptoms or conditions is deemed ineffective: chronic disease anemia, fever, depression, fatigue, rheumatoid nodules, vasculitis, neuropathy, scleritis, pericarditis, Felty's syndrome and/or joint destruction.

A detectable improvement can also be detected using the American College of Rheumatism (ACR) rheumatoid arthritis classification criteria. For example a 20% (ACR20), 50% (ACR50) or 70% (ACR70) improvement from baseline can be used to show detectable improvement.

The disease activity score (DAS28) can be used to show detectable improvement. DAS28 is a composite score of tender joints count based on 28 joints, a swollen joints count based on 28 joints, a general health assessment and a marker of inflammation which can be assessed by measuring C-reactive protein (CRP) levels. The disease response can be presented using the European League against Rheumatism (EULAR) response criteria. A good response by this criteria is an improvement of greater than 1.2 in DAS28 score with a present score of greater than or equal to 3.2. A moderate response is an improvement of greater than 0.6 but less than or equal to 1.2 in DAS28 score and a present score of greater than 3.2. Non-response is an improvement of less than 0.6 in DAS28 score and a present score of greater than 5.1. DAS28 remission is a DAS28 score of less than 2.6. A detectable improvement can also be shown by measuring an improvement in any of the components of the DAS28 score.

EXAMPLES

Example 1. Combination of Sarilumab and Methotrexate is Effective in Treatment of Rheumatoid Arthritis in Patients where Methotrexate Treatment is Ineffective A worldwide, double-blind, placebo-controlled, randomized study was performed in patients with rheumatoid arthritis with an inadequate response to methotrexate (MTX). Patients who were included in the study had the following criteria. Patients needed to have active disease defined as: at least 6 of 66 swollen joints and 8 of 68 tender joints and; hs-CRP>6 mg/L. Patients also needed to have had continuous treatment with methotrexate (MTX)—10 to 25 mg/wk (or 6 to 25 mg/wk for patients within Asia-Pacific region for 12 weeks.

The study includes two parts. The first part (Part A) of the study was a 12-week, 6-arm dose-ranging part intended to select the two best dose regimens based on efficacy (reduction in signs and symptoms) and safety. The second part (Part B) of the study is a 52-week part to confirm the efficacy and safety of these two selected dose regimens on reduction in signs and symptoms, inhibition of progression of structural damage, improvement in physical function, and induction of major clinical response.

The operationally seamless design nature of this study resides in the fact that Part B is starting to test patients just after the last patient was randomized in Part A without waiting for the dose selection based on its results. Thus part B patients belong to 2 distinct cohorts according to the time of their enrollment:

- Cohort 1 of patients randomized before the dose selection: these patients are randomized into six arms (as the ones of Part A). After dose selection, the patients randomized in the two selected doses and the placebo regimens continue the 52-week trial but those randomized in the three other arms are discontinued from the present study but proposed to join an open label extension (see LTS11210).
- Cohort 2 of patients randomized after the dose selection: these patients are randomized into three arms, the two selected ones and placebo.

Part A

Patients were assessed at a screening visit for confirmation of the diagnosis, disease activity, eligibility to the study and verification of concomitant therapy. Complete examination and laboratory tests including hematology, chemistry profile, lipid profile, liver enzymes and acute phase reactants, HbA1c, hepatitis B and C and serum pregnancy test for women of childbearing potential were performed. An ECG evaluation was also performed. A PPD test and QuantiFERON were performed to exclude any tuberculosis as well as a chest X-ray (if a documented negative X-ray performed in the last 3 months is not available).

After confirmation of eligibility, patients were randomized in a balanced manner, in this international multi-center, double-blind, parallel group placebo-controlled, 12-week study treatment of six arms of SAR153191 or placebo given subcutaneously weekly with MTX cotherapy. The doses are shown in FIG. 1.

Methothrexate was administered for each patient as it had been before the study. This was at 10 to 25 mg/wk, or 6 to 25 mg/wk for patients within Asia-Pacific region; Taiwan, South Korea, Malaysia, Philippines, Thailand, and India.

During the first visit, patients were reminded of the list of prohibited medications, and that they should continue taking MTX at their current stable dose until the end of the study with folic acid as per local recommendation to prevent MTX toxicity. The patients were trained to prepare and self administer the IMP and were reminded to have injection strictly 7 days apart. At dosing time points occurring outside site visits, SAR153191 was injected by the patient himself, by a trained professional caregiver or by a trained qualified person.

Patients had six additional visits at weeks 2, 4, 6, 8, 10, and 12. Efficacy assessment and laboratory test including hematology, chemistry profile, lipid profile, liver enzymes and acute phase reactants were assessed throughout the study to allow calculation of the main efficacy scores, and follow up of safety aspects. At randomization visit and at Week 2, 4, 8, and 12, a complete joint examination for tender joint count and swollen joint count was performed by an assessor independent from the Investigator and the patient's data, in order to calculate the ACR score (primary endpoint). In order to maintain the blind, the Investigator, the Sponsor and the patient will be blind to CRP and serum IL6 levels during the study.

A close monitoring of adverse events including potential infections assessed in part by monitoring of body temperature was performed at every visit. Presence of tuberculosis was checked through specific patient assessment (check for any signs or symptoms, or contact with active TB). Neurological abnormalities (history and physical examination) or autoimmune diatheses (ANA, ds-DNA antibodies) were tested at baseline and end of treatment visit.

Specific blood and urine samples were taken during the study to test potential biomarkers that may be predictive of disease response or adverse events. These included a single sample for DNA (after the patient has signed a specific informed consent form) and several samples obtained sequentially throughout the study for RNA expression-profiling and protein biomarker analyses. Samples were also collected at appropriate time points for pharmacokinetic parameters and antibody to SAR153191.

Patients prematurely discontinued were evaluated at an end of treatment visit with complete clinical and laboratory evaluation. They were considered as non-responders with regard to the ACR score.

At the end of treatment visit, all patients were scheduled to complete a Post Treatment Follow-up Visit. Patients who had completed the treatment period were proposed to enter an open-label long-term safety extension study with SAR153191.

Results

Human patients treated with sarilumab (REGN88/SAR153191) in combination with the standard RA treatment, methotrexate (MTX), achieved a significant and clinically meaningful improvement in signs and symptoms of moderate-to-severe rheumatoid arthritis (RA) compared to patients treated with MTX alone. The 306-patient, dose-ranging, multinational, randomized, multi-arm, double-blind, placebo-controlled study was performed that compared five different dose regimens of sarilumab in combination with MTX to placebo plus MTX. The primary endpoint of the study was the proportion of patients achieving at least a 20% improvement in RA symptoms (ACR20) after 12 weeks.

Figure 2:
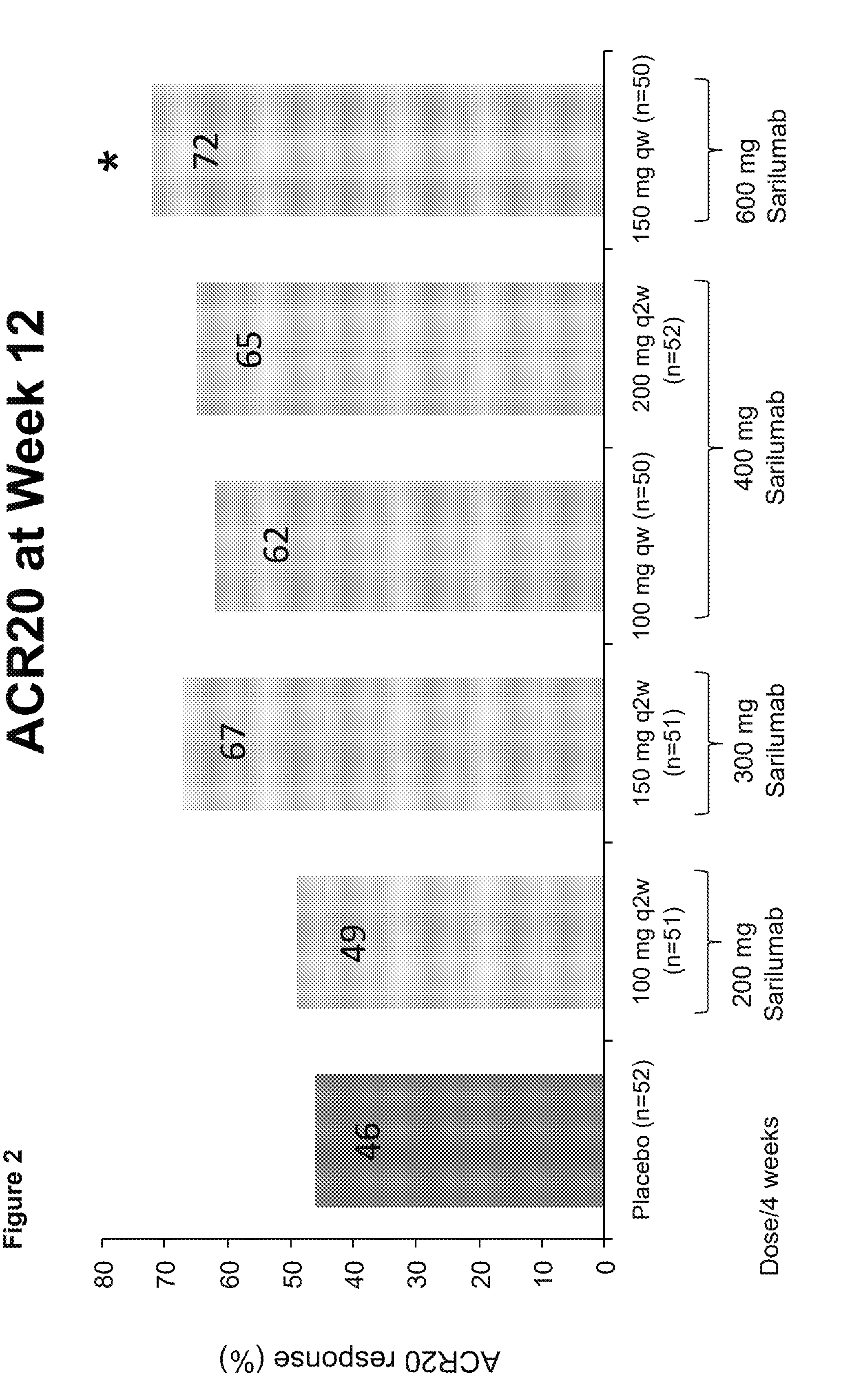
FIG. 2 depicts the clinical trial results regarding the primary endpoint of improved ACR20 response after 12 weeks in patients receiving one of 5 treatment arms of sarilumab/MTX co-therapy in comparison with placebo. Asterisk (*) indicates significance versus placebo by Cochran-Mantel-Haenszel test ($p<0.05$), correcting for multiplicity by Hommel's procedure.

A dose response was observed in patients receiving sarilumab in combination with MTX. An ACR20 response after 12 weeks was seen in 49.0% of patients receiving the lowest sarilumab dose regimen and 72.0% of patients receiving the highest dose regimen compared to 46.2% of patients receiving placebo and MTX (p=0.02, corrected for multiplicity, for the highest sarilumab dose regimen) (FIG. 2). The most common adverse events (>5%) reported more frequently in active-treatment arms included infections (non-serious), neutropenia, and liver-function test abnormalities. The types and frequencies of adverse events were consistent with those previously reported with IL-6 inhibition. The incidence of serious adverse events among the five sarilumab treatment groups and the placebo group were comparable.

Figure 3:
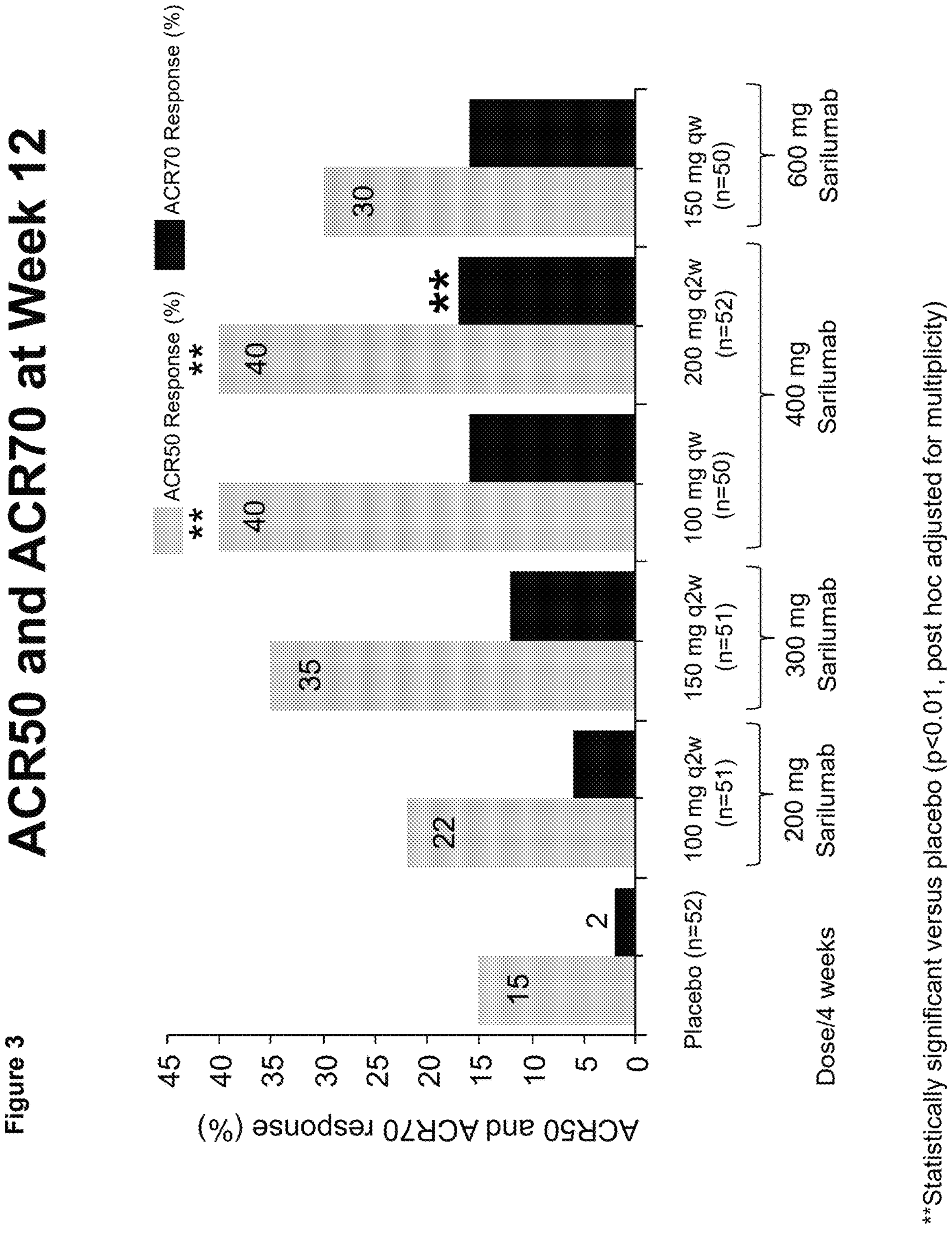
FIG. 3 depicts the clinical trial results regarding the secondary endpoint of improved ACR50 and ACR70 response after 12 weeks in patients receiving one of 5 treatment arms of sarilumab/MTX co-therapy in comparison with placebo. Double asterisk (**) indicates statistical significance versus placebo ($p<0.01$, post hoc adjusted for multiplicity).

Sarilumab also demonstrated significant benefit compared to placebo in secondary endpoints, including ACR 50, ACR 70, and DAS 28 scores, additional measures of clinical activity used in RA trials. More specifically:

An ACR50 response after 12 weeks was seen in 22% of patients receiving the lowest sarilumab dose regimen and 30% of patients receiving the highest dose regimen compared to 15% of patients receiving placebo and MTX (FIG. 3)

The ACR70 was also significantly higher in the 200 mg q2w group versus placebo. An ACR70 response after 12 weeks was seen in 16% of patients receiving the highest dose regimen compared to 2% of patients receiving placebo and MTX (FIG. 3).

These results provide evidence that IL-6R blockade with sarilumab represents a promising new anti-inflammatory investigational therapy for reducing RA disease symptoms.

Part B

Patients will be assessed at a screening visit for confirmation of the diagnosis disease activity, eligibility to the study and verification of concomitant therapy. The Investigator will check that the patient is either positive anticyclic citrullinated peptide antibody (CCP) or positive rheumatoid factor (RF) or that he/she has a confirmed bone erosion on an X-ray. If necessary, for patients who are both CCP and RF negative and have no X-ray, a centrally-reviewed screening X-ray will be performed and considered also as the baseline X-ray assessment for the study.

Cohort 1: Patients Randomized Before the Dose Selection.

Recruitment in for the long term safety extension study will start just after the last patient has been randomized in Part A. After confirmation of eligibility, patients will be randomized, in a balanced manner stratified by prior biologic use and by regions, in an international, multi-center, double-blind, parallel group placebo-controlled, study treatment of 6 arms of SAR153191 (5 active dose regimens) or placebo given subcutaneously weekly with MTX cotherapy.

At the beginning of every patient visit for Cohort 1 patients, the Investigator will check through IVRS list that the patient is still "eligible" for the study, i.e., that the patient is not to be discontinued because of randomization in a nonselected arm. Indeed, when the pivotal dose regimens are selected from Part A, only patients randomized in the corresponding arms or placebo will still be considered eligible for the study and will continue in the study for a total of 52 weeks. The other patients (randomized in the nonselected dose regimens) will be considered no longer eligible by IVRS. The Investigator will propose these patients to participate in an open extension study with SAR153191 at the highest dose regimen available at the time the patient is enrolled.

The initial randomization will remain blinded for all patients.

Cohort 2: Patients Randomized after the Dose Selection-Pivotal Part.

At day 1, after confirmation of eligibility, patients will be randomized, in a balanced manner stratified by prior biologic use and by regions, in an international, multi-center, double-blind, parallel group, placebo-controlled, study of 3 arms of SAR153191 (2 pivotal dose regimens) or placebo given subcutaneously with MTX cotherapy.

Both Cohorts:

In either cohort, patients will be evaluated at Week 2, at Week 4, and every 4 weeks until Week 28 and then every 8 weeks until Week 52 for efficacy and safety assessments and laboratory tests.

The same procedures as described in Part A will be applied in Part B. In addition, an X-ray evaluation of the hands and feet joints will be performed at baseline, Week 24 and Week 52. Radiographs de-identified of any patient information will be sent to central readers for calculation of the Sharp score (a specific scoring system of joints destruction). Health economic assessments will be also added such as SF-36.

From Week 16, patients with lack of efficacy defined as less than 20% improvement from baseline in either swollen joints count (SJC) or tender joints count (TJC) for 2 consecutive visits, or any other clear lack of efficacy based on Investigator judgment will be proposed to be rescued with open-label SAR153191 highest available dose at the time of transfer into the rescue treatment arm, and will continue in the study according to their planned visit schedule. Blood samples for laboratory analysis will be taken two weeks after the switch for safety purpose. They will be considered nonresponders for the primary endpoint (ACR20). These patients will stay in the study and continue all visits.

In selected countries, patients who meet lack of efficacy criteria at Part B treatment Visit 7/Week 16, or thereafter, will be permanently discontinued from treatment, and will not be eligible to participate in the open treatment rescue arm. Instead, the patients will have a follow-up visit to evaluate safety 6 weeks after the End of Treatment visit.

For any patient who discontinues prematurely or who is prematurely rescued with open SAR153191, an additional X-ray evaluation will be performed at the time of withdrawal or rescue, unless a study X-ray assessment has been performed within the preceding 3 months (a window of 3 months between 2 X-ray evaluations should be considered to avoid over X-ray exposure).

Patients completing Part B (including those in the open-label rescue arm) will be proposed to be rolled into an open label extension study at the maximum dose regimen at the time of enrollment. All patients will be scheduled to complete the Post Treatment Follow-up Visit. If the patient agrees to enter the SAR153191 open-label long-term extension study, and is confirmed to be eligible, the Post Treatment Follow-up Visit will not be completed.

Example 2. Combination of Sarilumab and DMARDs are Effective in Treatment of Rheumatoid Arthritis in Patients where TNF-α Antagonist and Methotrexate Treatment are Ineffective A worldwide, double-blind, placebo-controlled, randomized study was performed in patients with rheumatoid arthritis with an inadequate response to methotrexate (MTX) and at least one TNF-α antagonist. Patients who were included in the study had the following criteria. Patients had, in the opinion of the investigator, an inadequate response to at least one TNF-α antagonist, after being treated for at least 3 months in the last 2 years, or patients being intolerant to at least 1 TNF-α antagonist, resulting in discontinuation. TNF-α antagonists included etanercept, infliximab, adalimumab, golimumab and/or certolizumab pegol. Patients needed to have active disease defined as: at least 6 of 66 swollen joints and 8 of 68 tender joints and; hs-CRP ≥8 mg/L. Patients also needed to have had continuous treatment with one or a combination of DMARDs for at least 12 weeks prior to baseline and on a stable dose(s) for at least 6 weeks prior to screening. These DMARDs included methotrexate (MTX)—10 to 25 mg/wk (or 6 to 25 mg/wk for patients within Asia-Pacific region; leflunomide (LEF)—10 to 20 mg daily; sulfasalazine (SSZ)—1000 to 3000 mg daily; or hydroxychloroquine (HCQ)—200 to 400 mg daily.

TABLE 1

Groups and forms for both investigational medicinal product and noninvestigational medicinal product

| Group | Treatment | Sarilumab 150 mg | Sarilumab 200 mg | Placebo | Background medication as monotherapy or in combination |
|---|---|---|---|---|---|
| I | BT + sarilumab every 2 weeks (q2w) | 1 SC injection | | — | Including: Methotrexate-10 to 25 mg/wk (or 6 to 25 mg/wk for patients within Asia-Pacific region) with folic/folinic acid supplement Leflunomide-10 to 20 mg daily Sulfasalazin-1000 to 3000 mg daily Hydroxychloroquin-200 to 400 mg daily |
| II | BT + sarilumab q2w | — | 1 SC injection | — | Same as above |
| III | BT + placebo q2w | — | — | 1 SC injection | Same as above |

From Week 12 patients with lack of efficacy defined as less than 20% improvement from baseline in both swollen joint count and tender joint count for 2 consecutive visits will be proposed to be rescued with open label sarilumab at the highest dose in the trial. These patients will continue the trial according to the schedule of visits.
BT = background therapy;
q2w = every other week;
SC = subcutaneous from baseline in both SJC and TJC for 2 consecutive visits will be proposed to be rescued with open label sarilumab at the highest dose in the trial. These patients will continue the trial according to the schedule of visits.

In this study, sarilumab is administered on top of DMARD therapy, considered as a background therapy. All patients should continue to receive continuous treatment with one or a combination of nonbiologic DMARD(s) as background therapy for at least 12 weeks prior to baseline and on a stable dose(s) for at least 6 weeks prior to screening:

Subcutaneous administration will occur in the abdomen or thigh. Each dose will be self-administered (whenever possible), in a single injection. The SC injection sites can be alternated between the 4 quadrants of the abdomen (except the navel or waist area) or the thigh (front and side).

Patients and/or their nonprofessional caregivers will be trained to prepare and administer IMP at the start of the double-blind treatment period. This training must be documented in the patients' study file. The study coordinator or designee may administer the first injection comprising the initial dose as part of the training procedure on Day 1 (Visit 2). On days when the patient has a study visit, the IMP will be administered following clinic procedures and blood collection. For doses not given at the study site, diaries will be provided to record information pertaining to these injections; these diaries will be kept as source data in the patients' study file. If the patient is unable or unwilling to administer IMP, arrangements must be made for qualified site personnel and/or caregiver to administer IMP for the doses that are not scheduled to be given at the study site.

If the study visit is not performed at the site as scheduled, the dose will be administered by the patient and/or their caregiver(s) as scheduled.

Treatment will last for 24 weeks. From Week 12, patients with lack of efficacy defined as less than 20% improvement methotrexate (MTX)—10 to 25 mg/wk (or 6 to 25 mg/wk for patients within Asia-Pacific region) with folic/folinic acid supplement.

leflunomide (LEF)—10 to 20 mg daily sulfasalazin (SSZ)—1000 to 3000 mg daily.

hydroxychloroquin (HCQ)—200 to 400 mg daily

Each DMARD dose will be recorded throughout the study on the case report form. At any time, the DMARD dose can be reduced for safety or tolerability reason. Any change in dose and the start date of the new dose should be recorded on the e-CRF at every visit. DMARD(s) will not be dispensed or supplied by the Sponsor as an IMP.

All patients taking MTX will receive folic/folinic acid according to local recommendation in the country where the study is conducted. The dose, route and administration schedule of folic/folinic acid will be recorded with concomitant medications.

Sarilumab and matching placebo will be provided in identically matched glass prefilled syringes. Each prefilled syringe contains 1.14 mL of sarilumab (SAR153191) or matching placebo solution.

A list of treatment kit numbers will be generated. A randomization list will be generated by the interactive voice response system (IVRS). Both the randomization and treatment kit lists will be loaded into the IVRS.

The treatment kit numbers will be obtained by the Investigator at the time of patient randomization and subsequent patient scheduled visits via IVRS that will be available 24 hours a day.

In accordance with the double-blind design, Investigators will remain blinded to study treatment and will not have access to the randomization (treatment codes) except under circumstances described in Section 8.7.

Patients will be randomized to one of the treatment arms via a centralized randomization system using an IVRS. A patient will be considered randomized when the treatment number has been provided by the IVRS.

At the screening visit, Visit 1, the site coordinator will contact the IVRS to obtain a patient number for each patient who gives informed consent. Each patient will be allocated a patient number associated with the center and allocated in chronological order in each center.

The treatment assignment will be allocated to the patient according to the central randomization list via the IVRS stratified by region and number of previous anti-TNFs (1 versus >1). At Visit 2 (Day 1), after confirming the patient is eligible for entry into the treatment period, the site coordinator will contact the IVRS in order to receive the first treatment assignments (kit numbers). Patients will be randomized to receive either one of the 2 treatment arms of sarilumab or its matching placebo. The randomization ratio is 1:1:1 (sarilumab 150 mg:sarilumab 200 mg:matching placebo). At subsequent dispensation visits during the treatment period, the site coordinator will call IVRS to obtain the subsequent treatment kits assignment. A confirmation fax/e-mail will be sent to the site after each assignment.

A randomized patient is defined as a patient who is registered and assigned a randomization number from the IVRS, as documented from the IVRS log file. IMP will also be recorded and tracked on the center IMP inventory forms.

The compositions and methods of the present disclosure are not to be limited in scope by the specific embodiments describe herein. Indeed, various modifications of the invention in addition to those described herein will become apparent to those skilled in the art from the foregoing description. Such modifications are intended to fall within the scope of the appended claims.

The invention claimed is:

1. A method of improving at least one symptom of rheumatoid arthritis, the method comprising subcutaneously administering, to a subject who is determined to have rheumatoid arthritis and have had an inadequate response to a prior treatment with at least one Disease Modifying Antirheumatic Drug (DMARD) other than an IL-6R antagonist, a dose of about 150 mg to about 200 mg of a human antibody once every two weeks, wherein the human antibody specifically binds human interleukin-6 receptor (IL-6R) and comprises: three heavy chain complementarity determining regions (HCDRs) of a heavy chain variable region comprising the amino acid sequence of SEQ ID NO:2, and three light chain CDRs (LCDRs) of a light chain variable region comprising the amino acid sequence of SEQ ID NO: 3, and wherein an improvement in at least one symptom of rheumatoid arthritis is characterized in that the subject achieves at least a 20% improvement in an American College of Rheumatology (ACR) core set disease index after at least 12 weeks of treatment comprising the human antibody.

2. The method of claim 1, further comprising administering to the subject at least one DMARD selected from: methotrexate, sulfasalazine, hydroxychloroquine, and leflunomide.

3. The method of claim 2, wherein the human antibody and the at least one DMARD are administered together.

4. The method of claim 1, further comprising administering to the subject at least one DMARD comprising methotrexateis.

5. The method of claim 1, wherein the human antibody is administered at a dose of about 150 mg once every two weeks or about 200 mg once every two weeks.

6. The method of claim 1, wherein an improvement in at least one symptom of rheumatoid arthritis is characterized in that the subject achieves at least a 50% improvement in an ACR core set disease index after at least 12 weeks of treatment comprising the human antibody.

7. The method of claim 1, wherein an improvement in at least one symptom of rheumatoid arthritis is characterized in that the subject achieves at least a 70% improvement in an ACR core set disease index after at least 12 weeks of treatment comprising the human antibody.

8. The method of claim 1, wherein an improvement in at least one symptom of rheumatoid arthritis is characterized in that the subject achieves, at least 24 weeks of treatment comprising the human antibody:

at least a 20% improvement in an ACR core set disease index, at least a 50% improvement in an ACR core set disease index, or at least a 70% improvement in an ACR core set disease index.

9. A method of improving at least one symptom of rheumatoid arthritis, the method comprising subcutaneously administering, to a subject who is determined to have moderate-to-severe rheumatoid arthritis and have had an inadequate response to a prior treatment with at least one Disease Modifying Antirheumatic Drug (DMARD) other than an IL-6R antagonist, a dose of about 150 mg of a human antibody once every two weeks, wherein the human antibody specifically binds human interleukin-6 receptor (IL-6R) and comprises; three heavy chain complementarity determining regions (HCDRs) of a heavy chain variable region comprising the amino acid sequence of SEQ ID NO:2, and three light chain CDRs (LCDRs) of a light chain variable region comprising the amino acid sequence of SEQ ID NO:3, and wherein an improvement in at least one symptom of rheumatoid arthritis is characterized in that the subject achieves at least a 20% improvement in an ACR core set disease index after at least 12 weeks of treatment comprising the human antibody.

10. The method of claim 9, wherein an improvement in at least one symptom of rheumatoid arthritis is characterized in that the subject achieves at least a 50% improvement in an ACR core set disease index after at least 12 weeks of treatment comprising of the human antibody.

11. The method of claim 9, wherein an improvement in at least one symptom of rheumatoid arthritis is characterized in that the subject achieves at least a 70% improvement in an ACR core set disease index after at least 12 weeks of treatment comprising the human antibody.

12. The method of claim 9, wherein an improvement in at least one symptom of rheumatoid arthritis is characterized in that the subject achieves, after at least 24 weeks of treatment comprising the human antibody:

at least a 20% improvement in an ACR core set disease index, at least a 50% improvement in an ACR core set disease index, or at least a 70% improvement in an ACR core set disease index.

13. A method of improving at least one symptom of rheumatoid arthritis, the method comprising subcutaneously administering, to a subject who is determined to have moderate-to-severe rheumatoid arthritis and have had an inadequate response to a prior treatment with at least one Disease Modifying Antirheumatic Drug (DMARD), a dose of about 200 mg of a human antibody once every two weeks, wherein the human antibody specifically binds human interleukin-6 receptor (IL-6R) and comprises: three heavy chain complementarity determining regions (HCDRs) of a heavy chain variable region comprising the amino acid sequence of SEQ ID NO:2, and three light chain CDRs (LCDRs) of a light chain variable region comprising the amino acid sequence of SEQ ID NO:3, and wherein an improvement in at least one symptom of rheumatoid arthritis is characterized in that the subject achieves at least a 20% improvement in an ACR core set disease index after at least 12 weeks of treatment comprising the human antibody.

14. The method of claim 13, wherein an improvement in at least one symptom of rheumatoid arthritis is characterized in that the subject achieves at least a 50% improvement in an ACR core set disease index after at least 12 weeks of treatment comprising the human antibody.

15. The method of claim 13, wherein an improvement in at least one symptom of rheumatoid arthritis is characterized in that the subject achieves at least a 70% improvement in an ACR core set disease index after at least 12 weeks of treatment comprising the human antibody.

16. The method of claim 13, wherein an improvement in at least one symptom of rheumatoid arthritis is characterized in that the subject achieves, after at least 24 weeks of treatment comprising a dose of about 200 mg of the human antibody:

at least a 20% improvement in an ACR core set disease index, at least a 50% improvement in an ACR core set disease index, or at least a 70% improvement in an ACR core set disease index.

17. The method of claim 9, further comprising administering to the subject at least one DMARD selected from: methotrexate, sulfasalazine, hydroxychloroquine, and leflunomide.

18. The method of claim 13, further comprising administering to the subject at least one DMARD selected from: methotrexate, sulfasalazine, hydroxychloroquine, and leflunomide.

19. The method of claim 9, further comprising administering to the subject at least one DMARD comprising methotrexate.

20. The method of claim 13, further comprising administering to the subject at least one DMARD comprising methotrexate.

21. The method of claim 1, wherein the subject is determined to have rheumatoid arthritis and have had an inadequate response to a prior treatment with at least one DMARD comprising methotrexate.

22. The method of claim 1, wherein:

the human antibody comprises a heavy chain variable region comprising the amino acid sequence of SEQ ID NO: 2 and a light chain variable region comprising the amino acid sequence of SEQ ID NO: 3; or the human antibody is sarilumab.

23. The method of claim 9, wherein:

the human antibody comprises a heavy chain variable region comprising the amino acid sequence of SEQ ID NO: 2 and a light chain variable region comprising the amino acid sequence of SEQ ID NO: 3; or the human antibody is sarilumab.

24. The method of claim 13, wherein:

the human antibody comprises a heavy chain variable region comprising the amino acid sequence of SEQ ID NO: 2 and a light chain variable region comprising the amino acid sequence of SEQ ID NO: 3; or the human antibody is sarilumab.

* * * * *

```
                          SEQUENCE LISTING


<160> NUMBER OF SEQ ID NOS: 3

<210> SEQ ID NO 1
<211> LENGTH: 358
<212> TYPE: PRT
<213> ORGANISM: Homo sapiens
<220> FEATURE:
<221> NAME/KEY: MISC_FEATURE
<222> LOCATION: (1)..(358)
<223> OTHER INFORMATION: extracellular domain og human IL-6R

<400> SEQUENCE: 1

Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205
```

```
Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp
        355


<210> SEQ ID NO 2
<211> LENGTH: 116
<212> TYPE: PRT
<213> ORGANISM: Homo sapiens
<220> FEATURE:
<221> NAME/KEY: MISC_FEATURE
<222> LOCATION: (1)..(116)
<223> OTHER INFORMATION: heavy chain variable region of sarilumab

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser
        115


<210> SEQ ID NO 3
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: light chain variable region of sarilumab

<400> SEQUENCE: 3
```

-continued

| | | | | | | | | | | | | | | | |
|---|---|---|---|---|---|---|---|---|---|---|---|---|---|---|---|
| Asp | Ile | Gln | Met | Thr | Gln | Ser | Pro | Ser | Ser | Val | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Gln | Gly | Ile | Ser | Ser | Trp |
| | | | 20 | | | | | 25 | | | | | 30 | | |
| Leu | Ala | Trp | Tyr | Gln | Gln | Lys | Pro | Gly | Lys | Ala | Pro | Lys | Leu | Leu | Ile |
| | | 35 | | | | | 40 | | | | | 45 | | | |
| Tyr | Gly | Ala | Ser | Ser | Leu | Glu | Ser | Gly | Val | Pro | Ser | Arg | Phe | Ser | Gly |
| | 50 | | | | | 55 | | | | | 60 | | | | |
| Ser | Gly | Ser | Gly | Thr | Asp | Phe | Thr | Leu | Thr | Ile | Ser | Ser | Leu | Gln | Pro |
| 65 | | | | | 70 | | | | | 75 | | | | | 80 |
| Glu | Asp | Phe | Ala | Ser | Tyr | Tyr | Cys | Gln | Gln | Ala | Asn | Ser | Phe | Pro | Tyr |
| | | | | 85 | | | | | 90 | | | | | 95 | |
| Thr | Phe | Gly | Gln | Gly | Thr | Lys | Leu | Glu | Ile | Lys | | | | | |
| | | | 100 | | | | | 105 | | | | | | | |